US008658169B2

(12) United States Patent
Matthews et al.

(10) Patent No.: US 8,658,169 B2
(45) Date of Patent: Feb. 25, 2014

(54) ANTIBODIES AGAINST IL-25

(75) Inventors: David John Matthews, London (GB);
Jillian Barlow, Cambridge (GB);
Andrew Neil James McKenzie,
Cambridge (GB)

(73) Assignee: Medical Research Council, London (GB)

( * ) Notice: Subject to any disclaimer, the term of this patent is extended or adjusted under 35 U.S.C. 154(b) by 69 days.

(21) Appl. No.: 13/121,898

(22) PCT Filed: Sep. 30, 2009

(86) PCT No.: PCT/IB2009/007302
§ 371 (c)(1),
(2), (4) Date: Jun. 13, 2011

(87) PCT Pub. No.: WO2010/038155
PCT Pub. Date: Apr. 8, 2010

(65) Prior Publication Data
US 2011/0250195 A1    Oct. 13, 2011

Related U.S. Application Data

(60) Provisional application No. 61/101,293, filed on Sep. 30, 2008.

(30) Foreign Application Priority Data

Sep. 30, 2008 (GB) .................................. 0817891.5

(51) Int. Cl.
*A61K 39/00* (2006.01)
*A61K 39/395* (2006.01)
*C07K 16/00* (2006.01)
*C07K 16/24* (2006.01)
*C12N 1/21* (2006.01)
*C12N 5/10* (2006.01)
*C12N 15/13* (2006.01)
*C12N 15/63* (2006.01)

(52) U.S. Cl.
USPC ................. 424/133.1; 424/130.1; 424/135.1; 424/139.1; 424/141.1; 424/142.1; 424/145.1; 424/158.1; 530/387.1; 530/387.3; 530/387.9; 530/388.1; 530/388.15; 530/388.23; 536/23.53; 435/69.1; 435/320.1; 435/325; 435/252.3

(58) Field of Classification Search
None
See application file for complete search history.

(56) References Cited

U.S. PATENT DOCUMENTS

| | | | |
|---|---|---|---|
| 8,206,717 B2 | 6/2012 | McKenzie et al. | |
| 2003/0008815 A1 | 1/2003 | Chen et al. | |
| 2010/0129380 A1 | 5/2010 | McKenzie et al. | |
| 2011/0318353 A1* | 12/2011 | Almagro et al. | 424/139.1 |

FOREIGN PATENT DOCUMENTS

| | | |
|---|---|---|
| WO | WO 92/01047 A1 | 1/1992 |
| WO | WO 2004/094473 A2 | 11/2004 |
| WO | WO 2006/094384 A1 | 9/2006 |
| WO | WO 2007/044450 A2 | 4/2007 |
| WO | WO 2008/129263 A1 | 10/2008 |
| WO | WO 2010/038155 A2 | 4/2010 |
| WO | WO 2011/123507 A1 * | 10/2011 |

OTHER PUBLICATIONS

Rudikoff et al. (Proc Natl Acad Sci USA, 1982; 79(6):1979-1983.*
Szefler, 2013, J Allergy Clin Immunol 131:36-26.*
Angkasekwinai, P., et al., "Interleukin 25 Promotes the Initiation of Proallergic Type 2 Responses," *JEM*, 204(7):1509-1517 (Jul. 2007).
Angkasekwinai, P., et al., "The Role of Il-25 in Airway Allergic Response," *J Allergy Clin Immunol*, 119(1):S134 (Jan. 2007). (From *J Allergy Clin Immunol*, Jan. 2007, Abstract No. 530).
Budelsky, A.L., et al., "Transgenic Mice Overexpressing Human IL-17E Exhibit an Asthma-Like Phenotype that is Exacerbated in an Ovalbumin-Induced Model of Asthma," *J Allergy Clin Immunol*, 117(2):S253 (Feb. 2006). (From *J Allergy Clin Immunol*, Feb. 2006, Abstract No. 980).
Fallon, P.G., et al., "Identification of an Interleukin (IL-)25-Dependent Cell Population that Provides IL-4, IL-5, and IL-13 at the Onset of Helminth Expulsion," *JEM*, 203(4):1105-1116 (Apr. 2006).
Fort, M.M., et al., "IL-25 Induces IL-4, IL-5, and IL-13 and Th2-Associated Pathologies In Vivo," *Immunity*, 15(6):985-995 (Dec. 2001).
Kawaguchi, M., et al., "IL-17 Cytokine Family," *J Allergy Clin Immunol*, 114(6):1265-1273 (Dec. 2004).
Létuvé, S., et al., "IL-17E Upregulates the Expression of Proinflammatory Cytokines in Lung Fibroblasts," *J Allergy Clin Immunol*, 117(3):590-596 (Mar. 2006).
Little, M., et al., "Of Mice and Men: Hybridoma and Recombinant Antibodies," *Immunology Today*, 21(8):364-370 (Aug. 2000).
Marks, J.D., et al., "By-Passing Immunization. Human Antibodies from V-Gene Libraries Displayed on Phage," *Mol Biol*, 222(3):581-597 (Dec. 1991).
Owyang, A.M., et al., "Interleukin 25 Regulates Type 2 Cytokine-Dependent Immunity and Limits Chronic Inflammation in the Gastrointestinal Tract," *JEM*, 203(4):843-849 (Apr. 2006).
R&D Systems, "Monoclonal Anti-Human IL-17E Antibody," [online], Mar. 2007 [retrieved on Jul. 24, 2007]. Retrieved from the Internet URL: http://www.rndssystems.com/pdf/mab1258.pdf.
Sharkhuu, T., et al., "Mechanism of Interleukin-25 (IL-17E)-Induced Pulmonary Inflammation and Airways Hyper-Reactivity," *Clinical and Experimental Allergy*, 36(12):1575-1583 (Dec. 2006).

(Continued)

*Primary Examiner* — Elizabeth C Kemmerer
(74) *Attorney, Agent, or Firm* — Hamilton, Brook, Smith & Reynolds, P.C.

(57) ABSTRACT

The present invention relates to IL-25 antibody VH domains and target binding members (e.g., antibodies) that comprise such antibody VH domains and bind IL-25. The invention also relates to compositions comprising target binding members {e.g., antibodies) that bind IL-25, methods of producing such target binding members, and uses of such target binding members for the treatment or prevention of diseases and conditions (e.g., asthma, inflammatory bowel disease).

32 Claims, 14 Drawing Sheets

(56) References Cited

OTHER PUBLICATIONS

Tamachi, T., et al., "IL-25 Enhances Allergic Airway Inflammation by Amplifying a $T_H2$ Cell-Dependent Pathway in Mice," *J Allergy Clin Immunol*, 118(3):606-614 (Sep. 2006).

International Search Report (6 pages) issued in International Application No. PCT/GB2008/001365, dated Aug. 14, 2008.

International Preliminary Report on Patentability (8 pages) issued in International Application No. PCT/GB2008/001365, dated Oct. 20, 2009.

Three Month Office Action, U.S. Appl. No. 12/596,053, dated Jun. 7, 2011.

Final Office Action, U.S. Appl. No. 12/596,053, dated Nov. 10, 2011.

Chen, Y., et al., "Selection and Analysis of an Optimized Anti-VEGF Antibody: Crystal Structure of an Affinity-matured Fab in Complex with Antigen," *J. Mol. Biol.*, 293: 865-881 (1999).

Vajdos, F.F., et al., "Comprehensive Functional Maps of the Antigen-binding Site of an Anti-ErbB2 Antibody Obtained with Shotgun Scanning Mutagenesis," *J. Mol. Biol.*, 320: 415-428 (2002).

MacCallum, R.M., et al., "Antibody-antigen Interactions: Contact Analysis and Binding Site Topography," *J. Mol. Biol.*, 262: 732-745 (1996).

Casset, F., et al., "A peptide mimetic of an anti-CD4 monoclonal antibody by rational design," *Biochemical and Biophysical Research Communication*, 307: 198-205 (2003). Available on line at www.sciencedirect.com.

Holm, P., et al., "Functional mapping and single chain construction of the anti-cytokeratin 8 monoclonal antibody TS1," *Molecular Immunology*, 44: 1075-1084 (2007). Available online at www.sciencedirect.com.

Paul, W.E., MD., "Structure and Function of Immunoglobulins," *Fundamental Immunology*, Third Edition, Chapter 9: 292-295 (1993).

Notification of Transmittal of the International Search Report and the Written Opinion of the International Searching Authority for Int'l Application No. PCT/IB2009/007302; Date Mailed: Apr. 8, 2010.

Notification Concerning Transmittal of International Preliminary Report on Patentability for Int'l Application No: PCT/IB2009/007302; Date Mailed: Apr. 14, 2011.

Almagro, J.C. and Fransson, J., "Humanization of Antibodies," *Fronteirs in Bioscience*, 13(1): 1619-1633 (Jan. 1, 2008), XP009126790.

Ballantyne, S. J., et al., "Blocking IL-25 Prevents Airway Hyper-responsiveness in Allergic Asthma," *Journal of Allergy and Clinical Immunology*, 120(6): 1324-1331 (Dec. 1, 2007), XP022383425.

Dall'Acqua, W.F., et al., "Antibody Humanization by Framework Shuffling," *Methods*. 36(1): 43-60 (May 1, 2005), XP004852552.

Davies, J. and Riechmann, L , "Affinity Improvement of Single Antibody VH Domains: Residues in All Three Hypervariable Regions Affect Antigen Binding," *Immunotechnology*, 2(3): 169-179 (Sep. 1, 1996), XP004070292.

Holt, L. J., et al., "Domain Antibodies: Proteins for Therapy" *Trends in Biotechnology*, 21(11): 484-490 (Nov. 1, 2003), XP004467495.

Lazar, G.A., et al., "A Molecular Immunology Approach to Antibody Humanization and Functional Optimization," *Molecular Immunology*, 44(8): 1986-1998 (Mar. 1, 2007), XP002540093.

Search Report and Written Opinion, Singapore Application No. 201102198-7 "Antibodies Against IL-25" filed Sep. 30, 2009, Matthews et al., dated Jun. 26, 2012.

Hurst, S.D., et al., "New IL-17 Family Members Promote Th1 or Th2 Responses in the Lung: In Vivo Function of the Novel Cytokine IL-25," *The Journal of Immunology*, 169: 443-453 (2002).

\* cited by examiner

Figure 1 The kappa light chain sequence of 2c3 mouse antibody. The CDRs are labelled.

```
5'  GACATCCAGATGACCCAGACCACCTCCAGCCTGAGCGCCAGCCTGGGCGACCGGGTGACCATCAGCTGCAGCGCCTCCCAGGGCATCAGC
                                                                                                  90
3'  CTGTAGGTCTACTGGGTCTGGTGGAGGTCGGACTCGCGGTCGGACCCGCTGGCCCACTGGTAGTCGACGTCGCGGAGGGTCCCGTAGTCG

1   D  I  Q  M  T  Q  T  T  S  S  L  S  A  S  L  G  D  R  V  T  I  S  C  S  A  S  Q  G  I  S

5'  AACTACCTGAACTGGTATCAGCAGAAGGCCGACGGCACCGTCGAGCTGCTGATCTACTACACCAGCAGCCTGCACAGCGGCGTGCCCAGC
                                                                                                  180
3'  TTGATGGACTTGACCATAGTCGTCTTCCGGCTGCCGTGGCAGCTCGACGACTAGATGATGTGGTCGTCGGACGTGTCGCCGCACGGGTCG

1   N  Y  L  N  W  Y  Q  Q  K  A  D  G  T  V  E  L  L  I  Y  Y  T  S  S  L  H  S  G  V  P  S

5'  CGGTTTAGCGGCAGCGGCTCCGGCACCGACTACAGCCTGACCATCTCCAACCTGGAACCCGAGGATATCGCCACCTACTACTGCCAGCAG
                                                                                                  270
3'  GCCAAATCGCCGTCGCCGAGGCCGTGGCTGATGTCGGACTGGTAGAGGTTGGACCTTGGGCTCCTATAGCGGTGGATGATGACGGTCGTC

1   R  F  S  G  S  G  S  G  T  D  Y  S  L  T  I  S  N  L  E  P  E  D  I  A  T  Y  Y  C  Q  Q

5'  TACAGCAAGCTGCCCTACACCTTTGGCGGCGGAACAAAGCTGGAAATCAAG
                                                                                                  321
3'  ATGTCGTTCGACGGGATGTGGAAACCGCCGCCTTGTTTCGACCTTTAGTTC

1   Y  S  K  L  P  Y  T  F  G  G  G  T  K  L  E  I  K
```

Figure 2 The heavy chain sequence of 2c3 mouse antibody. The CDRs are labelled.

```
5'  ATGGTGCTGTCCCTGCTGTACCTGCTGACCGCCCTGCCCGGCATCCTGAGCGAGGTGCAGCTGCAGCAGAGCGGCCCTGA
                                                                                         80
3'  TACCACGACAGGGACGACATGGACGACTGGCGGGACGGGCCGTAGGACTCGCTCCACGTCGACGTCGTCTCGCCGGGACT

M  V  L  S  L  L  Y  L  L  T  A  L  P  G  I  L  S  E  V  Q  L  Q  Q  S  G  P  E

5'  GCTGGTGAAGCCTGGCGCCAGCATGAAGATCAGCTGCAAGGCCAGCGGCTACAGCTTCACCGACTACACCATGAACTGGG
                                                                                         160
3'  CGACCACTTCGGACCGCGGTCGTACTTCTAGTCGACGTTCCGGTCGCCGATGTCGAAGTGGCTGATGTGGTACTTGACCC

L  V  K  P  G  A  S  M  K  I  S  C  K  A  S  G  Y  S  F  T  D  Y  T  M  N  W

5'  TGAAGCAGAGCCACGGCAAGAACCTGGAATGGATCGGCCTGATCAACCCCTACAACGGCGGCACCAGCTACAACCAGAAC
                                                                                         240
3'  ACTTCGTCTCGGTGCCGTTCTTGGACCTTACCTAGCCGGACTAGTTGGGGATGTTGCCGCCGTGGTCGATGTTGGTCTTG

V  K  Q  S  H  G  K  N  L  E  W  I  G  L  I  N  P  Y  N  G  G  T  S  Y  N  Q  N

5'  TTCAAGGGCAAGGCCACCCTGACCGTGGACAAGAGCAGCAGCACCGCCTACATGGAACTGCTGTCTCTGACCAGCGAGGA
                                                                                         320
3'  AAGTTCCCGTTCCGGTGGGACTGGCACCTGTTCTCGTCGTCGTGGCGGATGTACCTTGACGACAGAGACTGGTCGCTCCT

F  K  G  K  A  T  L  T  V  D  K  S  S  S  T  A  Y  M  E  L  L  S  L  T  S  E  D

5'  CAGCGCCGTGTACTACTGCGCCAGAGAGGGCTACGACGGCTACCTGTACTTCGCCATGGACTACTGGGGCCAGGGCACCA
                                                                                         400
3'  GTCGCGGCACATGATGACGCGGTCTCTCCCGATGCTGCCGATGGACATGAAGCGGTACCTGATGACCCCGGTCCCGTGGT

S  A  V  Y  Y  C  A  R  E  G  Y  D  G  Y  L  Y  F  A  M  D  Y  W  G  Q  G  T

5'  GCGTGACCGTGAGCAGC
                                                                                         417
3'  CGCACTGGCACTCGTCG

S  V  T  V  S  S
```

Figure 3 DNA and amino acid sequence of AY393094.

```
5'  ctcctcctggctgttctccaaggagtctgtgccgaggtgcgccttgtgcagtctggagcagaggtgaaaaagccgggggagtctctgaagatctcctgta
                                                                                                          100
3'  gaggaggaccgacaagaggttcctcagacacggctccacgcggaacacgtcagacctcgtctccacttttccggcccccctcagagacttctagaggacat 1    L  L  L  A  V  L  Q  G  V  C  A  E  V  R  L  V  Q  S  G  A  E  V  K  K  P  G  E  S  L  K  I  S  C 5'  aggcttctggatacagttttaccagtaactggatcggctgggtgcgccagatgcccgggaaaggcctggagtggattgggatcatctttcctggtgactc
                                                                                                          200
3'  tccgaagacctatgtcaaaatggtcattgacctagccgacccacgcggtctacgggccctttccggacctcacctaaccctagtagaaaggaccactgag 1    K  A  S  G  Y  S  F  T  S  N  W  I  G  W  V  R  Q  M  P  G  K  G  L  E  W  I  G  I  I  F  P  G  D  S 5'  tgataccatatacagcccgtccttccaaggccaggtcaccatttcagtcgacaagtccatcaataccgcctacctgcagtggagcagcctgaaggccacg
                                                                                                          300
3'  actatggtatatgtcgggcaggaaggttccggtccagtggtaaagtcagctgttcaggtagttatggcggatggacgtcacctcgtcggacttccggtgc 1    D  T  I  Y  S  P  S  F  Q  G  Q  V  T  I  S  V  D  K  S  I  N  T  A  Y  L  Q  W  S  S  L  K  A  T 5'  gacaccgccatgtattactgtgcgagacagaaccccccgagtatagtggcgcatatcatgatgggtggttcgacccctggggccagggaaccctggtca
                                                                                                          400
3'  ctgtggcggtacataatgacacgctctgtcttgggggggctcatatcaccgcgtatagtactacccaccaagctggggaccccggtcccttgggaccagt 1    D  T  A  M  Y  Y  C  A  R  Q  N  P  P  E  Y  S  G  A  Y  H  D  G  W  F  D  P  W  G  Q  G  T  L  V 5'  tcgtctcctca
                                                                                                          411
3'  agcagaggagt

1    I  V  S  S
```

Figure 4 DNA and amino acid sequence of humanised 2c3 RHA.

```
5'   ATGGGGTCAACCGCCATCCTTGGCctcctcctggctgttctccaaggagtctgtgccgaAgtgcgccttgtgcagtctggagcagaAgtg
0    ++++|++++|++++|++++|++++|++++|++++|++++|++++|++++|++++|++++|++++|++++|++++|++++|++++|++++    90
3'   TACCCCAGTTGGCGGTAGGAACCGgaggaggaccgacaagaggttcctcagacacggctTcacgcggaacacgtcagacctcgtctTcac 1    M  G  S  T  A  I  L  G  L  L  L  A  V  L  Q  G  V  C  A  E  V  R  L  V  Q  S  G  A  E  V 5'   aaaaagccggggagtctctgaagatctcTtgCaaggcttctggatacagttttaccGACTACACCATGAACtgggtgcgccagatgccc
0    ++++|++++|++++|++++|++++|++++|++++|++++|++++|++++|++++|++++|++++|++++|++++|++++|++++|++++    180
3'   tttttcggccccctcagagacttctagagAacGttccgaagacctatgtcaaaatggCTGATGTGGTACTTGacccacgcggtctacggg 1    K  K  P  G  E  S  L  K  I  S  C  K  A  S  G  Y  S  F  T  D  Y  T  M  N  W  V  R  Q  M  P 5'   gggaaaggcctggagtggattgggCTTATTAATCCTTACAATGGTGGTACTAGCTACAACCAGAAtTTCAAGGGCcaAgtcaccatttca
0    ++++|++++|++++|++++|++++|++++|++++|++++|++++|++++|++++|++++|++++|++++|++++|++++|++++|++++    270
3'   cccttccggacctcacctaacccGAATAATTAGGAATGTTACCACCATGATCGATGTTGGTCTTaAAGTTCCCGgtTcagtggtaaagt 1    G  K  G  L  E  W  I  G  L  I  N  P  Y  N  G  G  T  S  Y  N  Q  N  F  K  G  Q  V  T  I  S 5'   gtcgacaagtccatcaataccgcctacctgcagtggagcagcctgaaggccacggacaccgccatgtattactgtgcgagaGAGGgCTAT
0    ++++|++++|++++|++++|++++|++++|++++|++++|++++|++++|++++|++++|++++|++++|++++|++++|++++|++++    360
3'   cagctgttcaggtagttatggcggatggacgtcacctcgtcggacttccggtgcctgtggcggtacataatgacacgctctCTCCcGATA 1    V  D  K  S  I  N  T  A  Y  L  Q  W  S  S  L  K  A  T  D  T  A  M  Y  Y  C  A  R  E  G  Y 5'   GATGGTTACCTTTACTTTGCTATGGACTACtggggccagggaaccctggtcatcgtctccTCAG
0    ++++|++++|++++|++++|++++|++++|++++|++++|++++|++++|++++|++++|++++    424
3'   CTACCAATGGAAATGAAACGATACCTGATGaccccggtcccttgggaccagtagcagaggAGTC

1    D  G  Y  L  Y  F  A  M  D  Y  W  G  Q  G  T  L  V  I  V  S  S
```

Figure 5 DNA and amino acid sequence of AY510106.

```
5'  atgagggtccctgctcagctcctgggactcctgctgctctggctcccagataccagatgtgacatccagatgacccagtctccatcctccctgtctgcatctgtaggaga
                                                                                                                      110
3'  tactcccagggacgagtcgaggaccctgaggacgacgagaccgagggtctatggtctacactgtaggtctactgggtcagaggtaggagggacagacgtagacatcctct 1    M  R  V  P  A  Q  L  L  G  L  L  L  L  W  L  P  D  T  R  C  D  I  Q  M  T  Q  S  P  S  S  L  S  A  S  V  G  D 5'  cagagtcaccatcacttgccgggcgagtcagggcattagcaattatttagcctggtatcagcagaaaccagggaaagttcctaaactcctgatctatgctgcatccactt
                                                                                                                      220
3'  gtctcagtggtagtgaacggcccgctcagtcccgtaatcgttaataaatcggaccatagtcgtctttggtccctttcaaggatttgaggactagatacgacgtaggtgaa 1    R  V  T  I  T  C  R  A  S  Q  G  I  S  N  Y  L  A  W  Y  Q  Q  K  P  G  K  V  P  K  L  L  I  Y  A  A  S  T 5'  tgcaatcaggggtcccatctcggttcagcggcagtggatctgggacagatttcactctcaccatcagcagcctgcagcctgaagatgttgcaacttattactgtcaaaag
                                                                                                                      330
3'  acgttagtccccagggtagagccaagtcgccgtcacctagaccctgtctaaagtgagagtggtagtcgtcggacgtcggacttctacaacgttgaataatgacagttttc 1    L  Q  S  G  V  P  S  R  F  S  G  S  G  S  G  T  D  F  T  L  T  I  S  S  L  Q  P  E  D  V  A  T  Y  Y  C  Q  K 5'  tataacagtgccccgtacacttttggccaggggaccaagctggagatcaaa
                                                                                                                      381
3'  atattgtcacggggcatgtgaaaaccggtcccctggttcgacctctagttt

1    Y  N  S  A  P  Y  T  F  G  Q  G  T  K  L  E  I  K
```

Figure 6 The sequence of the humanised kappa light chain 2c3 RKA.

```
5'   atgagggtccctgctcagctcctgggactcctgctgctctggctcccagataccagatgtgacatccagatgacccagtctccatcctcc
                                                                                                    90
3'   tactcccagggacgagtcgaggaccctgaggacgacgagaccgagggtctatggtctacactgtaggtctactgggtcagaggtaggagg 1    M  R  V  P  A  Q  L  L  G  L  L  L  L  W  L  P  D  T  R  C  D  I  Q  M  T  Q  S  P  S  S 5'   ctgtctgcatctgtaggagacagagtcaccatcacttgcAGTGCAtccCAGGGCATTAGCAATTATCTgAAttggtatcagcagaaacca
                                                                                                    180
3'   gacagacgtagacatcctctgtctcagtggtagtgaacgTCACGTaggGTCCCGTAATCGTTAATAgAcTTaaccatagtcgtctttggt 1    L  S  A  S  V  G  D  R  V  T  I  T  C  S  A  S  Q  G  I  S  N  Y  L  N  W  Y  Q  Q  K  P 5'   gggaaagttcctaaactcctgatctatTACACATCAAGTTTACACTCAggggtcccatctcggttcagcggcagtggatctgggacagat
                                                                                                    270
3'   cccttctcaaggatttgaggactagataATGTGTAGTTCAAATGTGAGTcccagggtagagccaagtcgccgtcacctagaccctgtcta 1    G  K  V  P  K  L  L  I  Y  Y  T  S  S  L  H  S  G  V  P  S  R  F  S  G  S  G  S  G  T  D 5'   ttcactctcaccatcagcagcctgcagcctgaagatgttgcaacttattactgtCAGCAGTATAGcAAGCTgCCGTACACGtttggccag
                                                                                                    360
3'   aagtgagagtggtagtcgtcggacgtcggacttctacaacgttgaataatgacaGTCGTCATATCgTTCGAcGGCATGTGCaaaccggtc 1    F  T  L  T  I  S  S  L  Q  P  E  D  V  A  T  Y  Y  C  Q  Q  Y  S  K  L  P  Y  T  F  G  Q 5'   gggaccaagctggagatcaaa
                                                                                                    381
3'   ccctggttcgacctctagttt

1    G  T  K  L  E  I  K
```

Figure 7 Comparison of humanised antibody 2c3 RHA/RKA and variants with chimeric 2c3.

A

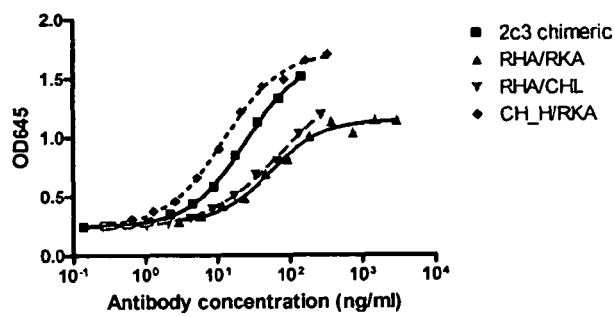

B

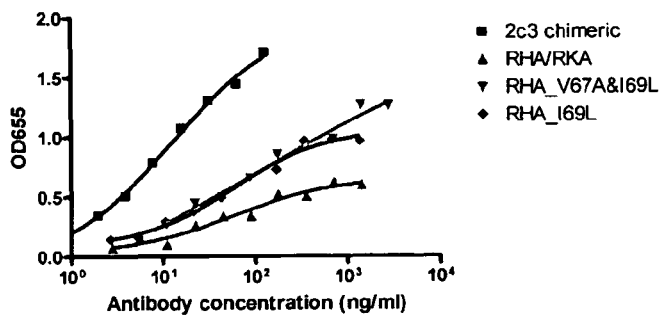

C

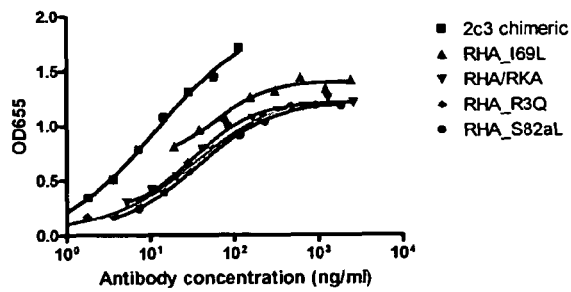

Comparison of IL-25 binding by recombinant 2c3 antibodies A. encoded by 2c3 RHA or 2c3 RKA co-expressed with chimeric 2c3 heavy chain (CH_H) or the 2c3 kappa light chain (CHL) compared with the fully chimeric 2c3 antibody (CH_H + CHL) B. encoded by 2c3 RHA mutants 2c3 RH_V67A&I69L or 2c3 RH_I69L co-transfected with 2c3 RKA and compared to chimeric 2c3 or unmutated humanised 2c3 RHA/RKA antibodies C. encoded by RHA mutants I69L, R3Q, S82aL co-transfected with 2c3 RKA and compared to the chimeric 2c3 or unmutated humanised 2c3 RHA/RKA antibodies. IL-25 binding was measured by ELISA.

Figure 8 Framework AJ399823 used in the design of humanised 2c3 RH2.

```
5'  gaggtgcagctggtggagtctgggggctgaggtgaagaagcctgggggcctcagtgaaagtttcgtgcaaggcttctggatactccttcagtagttatggta
                                                                                                              100
3'  ctccacgtcgaccacctcagaccccgactccacttcttcggaccccggagtcactttcaaagcacgttccgaagacctatgaggaagtcatcaataccat 1   E  V  Q  L  V  E  S  G  A  E  V  K  K  P  G  A  S  V  K  V  S  C  K  A  S  G  Y  S  F  S  S  Y  G 5'  tacattgggtgcgccaggccccggacaaaggcttgagtggatgggatggatcaacggtggcactggttttacaaaatattcacagaattttcagggcag
                                                                                                              200
3'  atgtaacccacgcggtccggggcctgtttccgaactcacctaccctacctagttgccaccgtgaccaaaatgttttataagtgtcttaaaagtcccgtc 1   I  H  W  V  R  Q  A  P  G  Q  R  L  E  W  M  G  W  I  N  G  G  T  G  F  T  K  Y  S  Q  N  F  Q  G  R 5'  agtcaccctaaccagggacacttccgcgagcacagcctacttggaactgaacagcctgagatctgaagacacgggtgtatattactgtgcgagggatccc
                                                                                                              300
3'  tcagtgggattggtccctgtgaaggcgctcgtgtcggatgaaccttgacttgtcggactctagacttctgtgcccacatataatgacacgctccctaggg 1    V  T  L  T  R  D  T  S  A  S  T  A  Y  L  E  L  N  S  L  R  S  E  D  T  G  V  Y  Y  C  A  R  D  P 5'  tacaataactacgcggcggaacttgactactggggccagggaaccctggtcaccgtctcctca
                                                                                                              363
3'  atgttattgatgcgccgccttgaactgatgaccccggtcccttgggaccagtggcagaggagt

1    Y  N  N  Y  A  A  E  L  D  Y  W  G  Q  G  T  L  V  T  V  S  S
```

Figure 9 Effect of specific CDR mutations to 2c3 RH2bcdef binding to IL-25.

A

B

The mutation of the 2c3 RH2bcdef heavy chain at two positions in its CDRs. HEK 293T cells were co transfected with either 2c3 RH2bcdef/RKA or 2c3 chimeric constructs plus A. CDR mutation at position 31 from aspartate to glycine (2c3 RH2bcdef_D31G) or B. CDR mutation at position 96 from glycine to aspartate. Binding to human IL-25 was measured by ELISA Figure 10 Effect on IL-25 binding by combining CDR mutations D31G and G96D.

■ RH2bcdef_G96D_D31G
▲ RH2bcdef_G96D

The humanised heavy chain 2c3 RH2bcdef was mutagenised and the mutants D31G and G96D were combined. HEK 293T cells were co transfected with either 2c3 RH2bcdef_G96D_D31G/RKA or 2c3 RH2bcdef_G96D/RKA and supernatants collected after 3 days. Antibody binding to human IL-25 was measured by ELISA.

Figure 11 Comparison of 2c3 RH2.5_S30T and 2c3 RH2.5_R71V binding to IL-25.

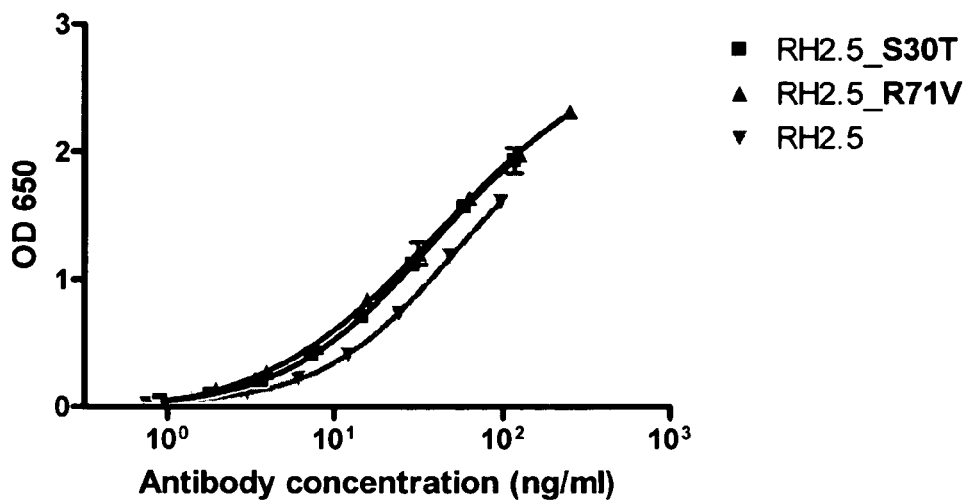

RH2.5 is the codon optimised version of RH2 plus the mutations D31G and G96D. The one remaining untested VCI residue, S30T, was examined and its binding to IL-25 by ELISA was compared with RH2.5_R71V and RH2.5. HEK 293T cells were co-transfected with the RH2.5_S30T or RH2.5_R71V or RH2.5 and the light chain construct RKA. After three days supernatants were harvested and

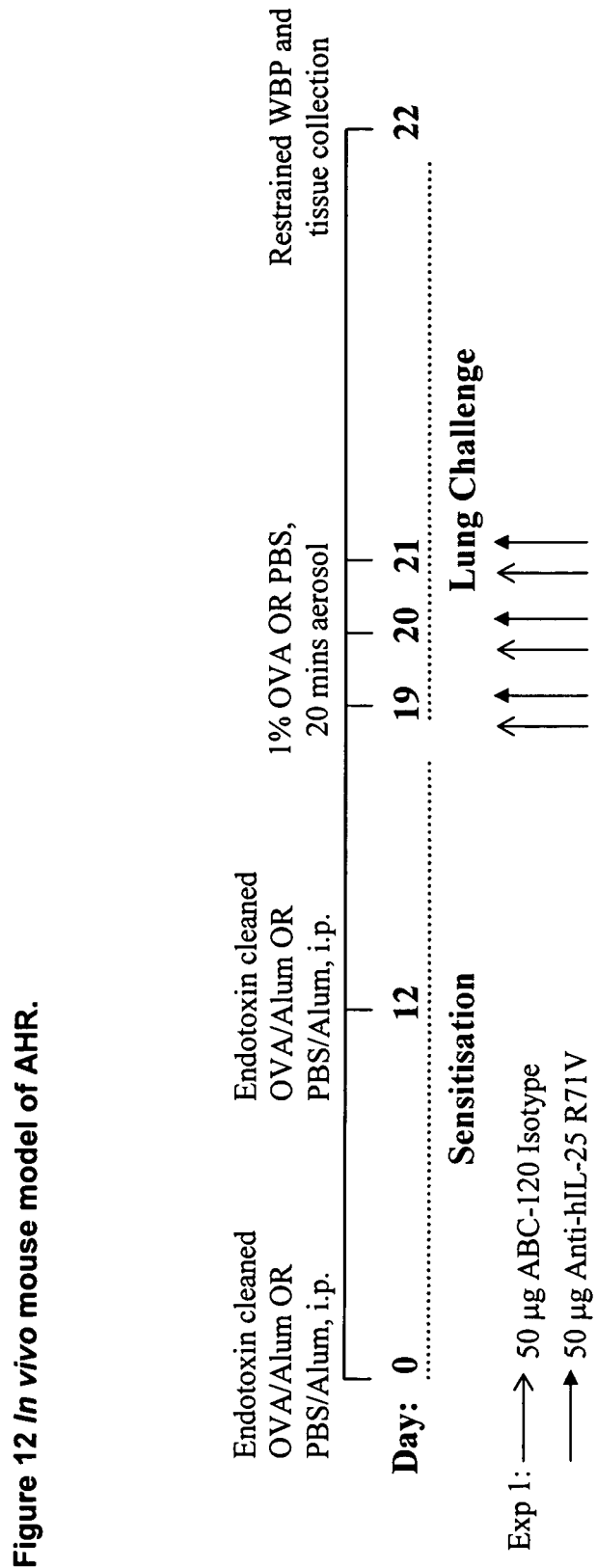
Figure 12 *In vivo* mouse model of AHR.

Figure 13 Effect of administering 2c3 RH2.5_R71V to pulmonary resistance in response to methacholine.

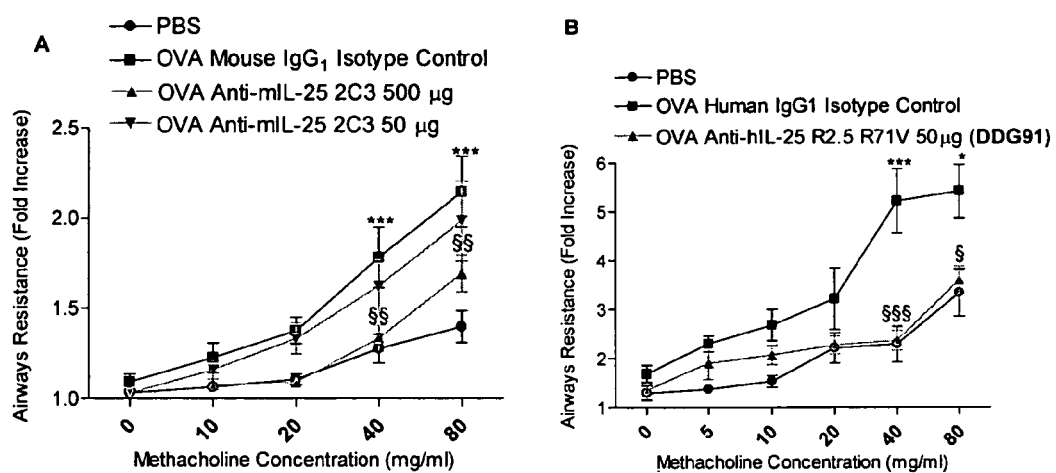

Treatment with anti-mIL-25 2c3 or anti-hIL-25 2c3 RH2.5 R71V during the lung challenge phase in an acute experimental mouse asthma model blocks AHR. Airways resistance was measured by restrained whole body plethysmography in response to PBS and then to increasing concentrations of methacholine. *(A)* Mice received anti-mIL-25 2c3 prior to each OVA aerosol challenge at either a 500 μg or a 50 μg dose. *(B)* Mice received anti-hIL-25 RH2.5 R71V prior to each OVA aerosol challenge at a 50 μg dose. A two way ANOVA with Bonferroni post-test was used to assess statistical differences. *, , and * denotes a significance value of $p=<0.05$, $p=<0.01$, and $p=<0.001$ between PBS and OVA $IgG_1$ isotype treated mice. §, §§, and §§§ denotes a significance value of $p=<0.05$, $p=<0.01$, and $p=<0.001$ between OVA $IgG_1$ isotype and anti-IL-25 treated mice.

Figure 14
A
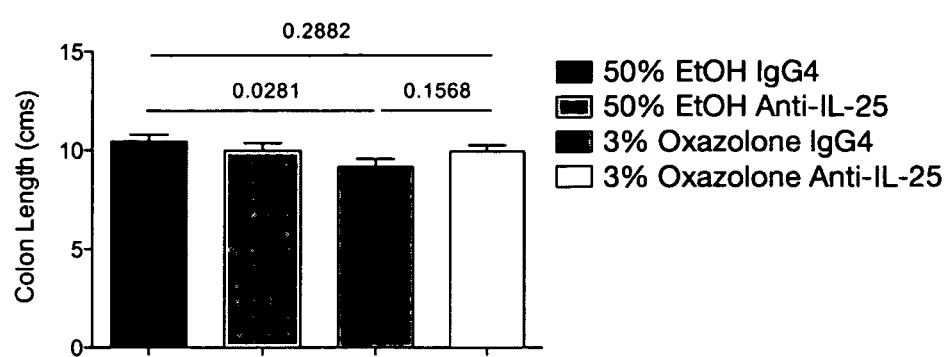
B
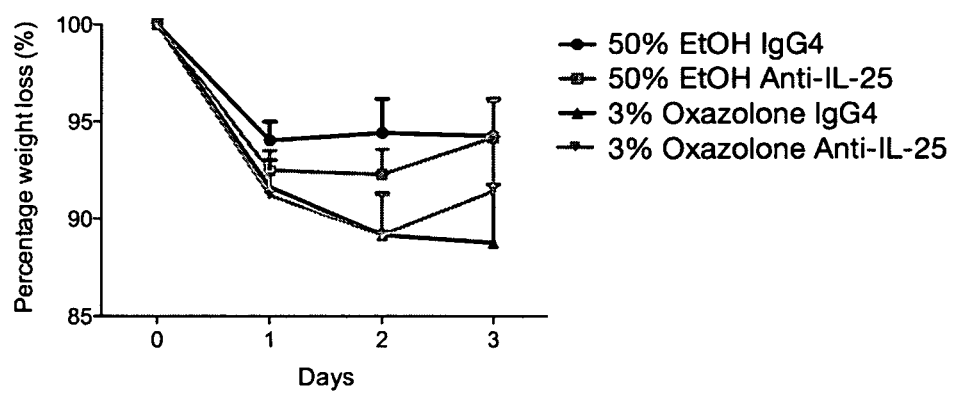

SEQUENCE LISTING

<160> NUMBER OF SEQ ID NOS: 41

<210> SEQ ID NO 1
<211> LENGTH: 122
<212> TYPE: PRT
<213> ORGANISM: Artificial Sequence
<220> FEATURE:
<223> OTHER INFORMATION: Synthetic sequence: Humanised VH domain

```
<220> FEATURE:
<221> NAME/KEY: VARIANT
<222> LOCATION: (30)...(30)
<223> OTHER INFORMATION: Xaa is Ser or Thr
<220> FEATURE:
<221> NAME/KEY: VARIANT
<222> LOCATION: (31)...(31)
<223> OTHER INFORMATION: Xaa is Gly, Asp, Ala, Ser, Val Asn, Lys, Tyr or
      Met
<220> FEATURE:
<221> NAME/KEY: VARIANT
<222> LOCATION: (48)...(48)
<223> OTHER INFORMATION: Xaa is Met or Ile
<220> FEATURE:
<221> NAME/KEY: VARIANT
<222> LOCATION: (72)...(72)
<223> OTHER INFORMATION: Xaa is Val or Arg
<220> FEATURE:
<221> NAME/KEY: VARIANT
<222> LOCATION: (100)...(100)
<223> OTHER INFORMATION: Xaa is Asp, Asn or Gly

<400> SEQUENCE: 1

Glu Val Gln Leu Val Glu Ser Gly Ala Glu Val Lys Lys Pro Gly Ala
 1               5                  10                  15

Ser Val Lys Val Ser Cys Lys Ala Ser Gly Tyr Ser Phe Xaa Xaa Tyr
            20                  25                  30

Thr Met Asn Trp Val Arg Gln Ala Pro Gly Gln Arg Leu Glu Trp Xaa
         35                  40                  45

Gly Leu Ile Asn Pro Tyr Asn Gly Gly Thr Ser Tyr Asn Gln Asn Phe
 50                  55                  60

Lys Gly Arg Val Thr Leu Thr Xaa Asp Thr Ser Ala Ser Thr Ala Tyr
 65                  70                  75                  80

Leu Glu Leu Asn Ser Leu Arg Ser Glu Asp Thr Gly Val Tyr Tyr Cys
             85                  90                  95

Ala Arg Glu Xaa Tyr Asp Gly Tyr Leu Tyr Phe Ala Met Asp Tyr Trp
             100                 105                 110

Gly Gln Gly Thr Leu Val Thr Val Ser Ser
            115                 120

<210> SEQ ID NO 2
<211> LENGTH: 122
<212> TYPE: PRT
<213> ORGANISM: Artificial Sequence
<220> FEATURE:
<223> OTHER INFORMATION: Synthetic sequence: Humanised VH domain
      RH2.5_R71V

<400> SEQUENCE: 2

Glu Val Gln Leu Val Glu Ser Gly Ala Glu Val Lys Lys Pro Gly Ala
 1               5                  10                  15

Ser Val Lys Val Ser Cys Lys Ala Ser Gly Tyr Ser Phe Ser Gly Tyr
            20                  25                  30

Thr Met Asn Trp Val Arg Gln Ala Pro Gly Gln Arg Leu Glu Trp Met
         35                  40                  45

Gly Leu Ile Asn Pro Tyr Asn Gly Gly Thr Ser Tyr Asn Gln Asn Phe
 50                  55                  60

Lys Gly Arg Val Thr Leu Thr Val Asp Thr Ser Ala Ser Thr Ala Tyr
 65                  70                  75                  80

Leu Glu Leu Asn Ser Leu Arg Ser Glu Asp Thr Gly Val Tyr Tyr Cys
             85                  90                  95

Ala Arg Glu Asp Tyr Asp Gly Tyr Leu Tyr Phe Ala Met Asp Tyr Trp
             100                 105                 110
```

```
Gly Gln Gly Thr Leu Val Thr Val Ser Ser
        115                 120
```

<210> SEQ ID NO 3
<211> LENGTH: 120
<212> TYPE: PRT
<213> ORGANISM: Artificial Sequence
<220> FEATURE:
<223> OTHER INFORMATION: Synthetic sequence: Humanised VH domain
      RH2.5_S30T

<400> SEQUENCE: 3

```
Glu Val Gln Leu Val Glu Ser Gly Ala Glu Val Lys Lys Pro Gly Ala
 1               5                  10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Arg Leu Glu Trp Met
        35                  40                  45

Gly Leu Ile Asn Pro Tyr Asn Gly Gly Thr Ser Tyr Asn Gln Asn Phe
    50                  55                  60

Lys Gly Arg Val Thr Leu Thr Arg Asp Thr Ser Ala Ser Thr Ala Tyr
65                  70                  75                  80

Leu Glu Leu Asn Ser Leu Arg Glu Asp Thr Gly Val Tyr Tyr Cys Ala
                85                  90                  95

Arg Glu Asp Tyr Asp Gly Tyr Leu Tyr Phe Ala Met Asp Tyr Trp Gly
            100                 105                 110

Gln Gly Thr Leu Val Val Ser Ser
        115                 120
```

<210> SEQ ID NO 4
<211> LENGTH: 122
<212> TYPE: PRT
<213> ORGANISM: Artificial Sequence
<220> FEATURE:
<223> OTHER INFORMATION: Synthetic sequence: Humanised VH domain RH2

<400> SEQUENCE: 4

```
Glu Val Gln Leu Val Glu Ser Gly Ala Glu Val Lys Lys Pro Gly Ala
1                5                  10                  15

Ser Val Lys Val Ser Cys Lys Ala Ser Gly Tyr Ser Phe Ser Gly Tyr
            20                  25                  30

Thr Met Asn Trp Val Arg Gln Ala Pro Gly Gln Arg Leu Glu Trp Met
        35                  40                  45

Gly Leu Ile Asn Pro Tyr Asn Gly Gly Thr Ser Tyr Asn Gln Asn Phe
    50                  55                  60

Lys Gly Arg Val Thr Leu Thr Arg Asp Thr Ser Ala Ser Thr Ala Tyr
65                  70                  75                  80

Leu Glu Leu Asn Ser Leu Arg Ser Glu Asp Thr Gly Val Tyr Tyr Cys
                85                  90                  95

Ala Arg Glu Asp Tyr Asp Gly Tyr Leu Tyr Phe Ala Met Asp Tyr Trp
            100                 105                 110

Gly Gln Gly Thr Leu Val Thr Val Ser Ser
        115                 120
```

<210> SEQ ID NO 5
<211> LENGTH: 122
<212> TYPE: PRT
<213> ORGANISM: Artificial Sequence
<220> FEATURE:
<223> OTHER INFORMATION: Synthetic sequence: Humanised VH domain

<400> SEQUENCE: 5

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Arg Leu Glu Trp Met
        35                  40                  45

Gly Leu Ile Asn Pro Tyr Asn Gly Gly Thr Ser Tyr Asn Gln Asn Phe
    50                  55                  60

Lys Gly Arg Val Thr Leu Thr Val Asp Thr Ser Ala Ser Thr Ala Tyr
65                  70                  75                  80

Leu Glu Leu Asn Ser Leu Arg Ser Glu Asp Thr Gly Val Tyr Tyr Cys
                85                  90                  95

Ala Arg Glu Asp Tyr Asp Gly Tyr Leu Tyr Phe Ala Met Asp Tyr Trp
            100                 105                 110

Gly Gln Gly Thr Leu Val Thr Val Ser Ser
        115                 120

<210> SEQ ID NO 6
<211> LENGTH: 122
<212> TYPE: PRT
<213> ORGANISM: Artificial Sequence
<220> FEATURE:
<223> OTHER INFORMATION: Synthetic sequence: Humanised VH domain

<400> SEQUENCE: 6

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Ser Phe Ser Asp Tyr
            20                  25                  30

Thr Met Asn Trp Val Arg Gln Ala Pro Gly Gln Arg Leu Glu Trp Met
        35                  40                  45

Gly Leu Ile Asn Pro Tyr Asn Gly Gly Thr Ser Tyr Asn Gln Asn Phe
    50                  55                  60

Lys Gly Arg Val Thr Leu Thr Val Asp Thr Ser Ala Ser Thr Ala Tyr
65                  70                  75                  80

Leu Glu Leu Asn Ser Leu Arg Ser Glu Asp Thr Gly Val Tyr Tyr Cys
                85                  90                  95

Ala Arg Glu Asp Tyr Asp Gly Tyr Leu Tyr Phe Ala Met Asp Tyr Trp
            100                 105                 110

Gly Gln Gly Thr Leu Val Thr Val Ser Ser
        115                 120

<210> SEQ ID NO 7
<211> LENGTH: 122
<212> TYPE: PRT
<213> ORGANISM: Artificial Sequence
<220> FEATURE:
<223> OTHER INFORMATION: Synthetic sequence: Humanised VH domain

<400> SEQUENCE: 7

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Thr Met Asn Trp Val Arg Gln Ala Pro Gly Gln Arg Leu Glu Trp Met
        35                  40                  45

Gly Leu Ile Asn Pro Tyr Asn Gly Gly Thr Ser Tyr Asn Gln Asn Phe

```
                    50                  55                  60
Lys Gly Arg Val Thr Leu Thr Arg Asp Thr Ser Ala Ser Thr Ala Tyr
 65                  70                  75                  80

Leu Glu Leu Asn Ser Leu Arg Ser Glu Asp Thr Gly Val Tyr Tyr Cys
                 85                  90                  95

Ala Arg Glu Asp Tyr Asp Gly Tyr Leu Tyr Phe Ala Met Asp Tyr Trp
                100                 105                 110

Gly Gln Gly Thr Leu Val Thr Val Ser Ser
            115                 120

<210> SEQ ID NO 8
<211> LENGTH: 122
<212> TYPE: PRT
<213> ORGANISM: Artificial Sequence
<220> FEATURE:
<223> OTHER INFORMATION: Synthetic sequence: Humanised VH domain

<400> SEQUENCE: 8

Glu Val Gln Leu Val Glu Ser Gly Ala Glu Val Lys Lys Pro Gly Ala
  1               5                  10                  15

Ser Val Lys Val Ser Cys Lys Ala Ser Gly Tyr Ser Phe Thr Asp Tyr
                 20                  25                  30

Thr Met Asn Trp Val Arg Gln Ala Pro Gly Gln Arg Leu Glu Trp Met
             35                  40                  45

Gly Leu Ile Asn Pro Tyr Asn Gly Gly Thr Ser Tyr Asn Gln Asn Phe
 50                  55                  60

Lys Gly Arg Val Thr Leu Thr Val Asp Thr Ser Ala Ser Thr Ala Tyr
 65                  70                  75                  80

Leu Glu Leu Asn Ser Leu Arg Ser Glu Asp Thr Gly Val Tyr Tyr Cys
                 85                  90                  95

Ala Arg Glu Asp Tyr Asp Gly Tyr Leu Tyr Phe Ala Met Asp Tyr Trp
                100                 105                 110

Gly Gln Gly Thr Leu Val Thr Val Ser Ser
            115                 120

<210> SEQ ID NO 9
<211> LENGTH: 122
<212> TYPE: PRT
<213> ORGANISM: Artificial Sequence
<220> FEATURE:
<223> OTHER INFORMATION: Synthetic sequence: Humanised VH domain

<400> SEQUENCE: 9

Glu Val Gln Leu Val Glu Ser Gly Ala Glu Val Lys Lys Pro Gly Ala
  1               5                  10                  15

Ser Val Lys Val Ser Cys Lys Ala Ser Gly Tyr Ser Phe Ser Gly Tyr
                 20                  25                  30

Thr Met Asn Trp Val Arg Gln Ala Pro Gly Gln Arg Leu Glu Trp Ile
             35                  40                  45

Gly Leu Ile Asn Pro Tyr Asn Gly Gly Thr Ser Tyr Asn Gln Asn Phe
 50                  55                  60

Lys Gly Arg Val Thr Leu Thr Val Asp Thr Ser Ala Ser Thr Ala Tyr
 65                  70                  75                  80

Leu Glu Leu Asn Ser Leu Arg Ser Glu Asp Thr Gly Val Tyr Tyr Cys
                 85                  90                  95

Ala Arg Glu Asp Tyr Asp Gly Tyr Leu Tyr Phe Ala Met Asp Tyr Trp
                100                 105                 110

Gly Gln Gly Thr Leu Val Thr Val Ser Ser
```

```
            115                 120

<210> SEQ ID NO 10
<211> LENGTH: 122
<212> TYPE: PRT
<213> ORGANISM: Artificial Sequence
<220> FEATURE:
<223> OTHER INFORMATION: Synthetic sequence: Humanised VH domain

<400> SEQUENCE: 10

Glu Val Gln Leu Val Glu Ser Gly Ala Glu Val Lys Lys Pro Gly Ala
 1               5                  10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Arg Leu Glu Trp Ile
        35                  40                  45

Gly Leu Ile Asn Pro Tyr Asn Gly Gly Thr Ser Tyr Asn Gln Asn Phe
    50                  55                  60

Lys Gly Arg Val Thr Leu Thr Arg Asp Thr Ser Ala Ser Thr Ala Tyr
65                  70                  75                  80

Leu Glu Leu Asn Ser Leu Arg Ser Glu Asp Thr Gly Val Tyr Tyr Cys
                85                  90                  95

Ala Arg Glu Asp Tyr Asp Gly Tyr Leu Tyr Phe Ala Met Asp Tyr Trp
            100                 105                 110

Gly Gln Gly Thr Leu Val Thr Val Ser Ser
        115                 120

<210> SEQ ID NO 11
<211> LENGTH: 122
<212> TYPE: PRT
<213> ORGANISM: Artificial Sequence
<220> FEATURE:
<223> OTHER INFORMATION: Synthetic sequence: Humanised VH domain

<400> SEQUENCE: 11

Glu Val Gln Leu Val Glu Ser Gly Ala Glu Val Lys Lys Pro Gly Ala
 1               5                  10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Arg Leu Glu Trp Ile
        35                  40                  45

Gly Leu Ile Asn Pro Tyr Asn Gly Gly Thr Ser Tyr Asn Gln Asn Phe
    50                  55                  60

Lys Gly Arg Val Thr Leu Thr Val Asp Thr Ser Ala Ser Thr Ala Tyr
65                  70                  75                  80

Leu Glu Leu Asn Ser Leu Arg Ser Glu Asp Thr Gly Val Tyr Tyr Cys
                85                  90                  95

Ala Arg Glu Asp Tyr Asp Gly Tyr Leu Tyr Phe Ala Met Asp Tyr Trp
            100                 105                 110

Gly Gln Gly Thr Leu Val Thr Val Ser Ser
        115                 120

<210> SEQ ID NO 12
<211> LENGTH: 122
<212> TYPE: PRT
<213> ORGANISM: Artificial Sequence
<220> FEATURE:
<223> OTHER INFORMATION: Synthetic sequence: Humanised VH domain

<400> SEQUENCE: 12
```

```
Glu Val Gln Leu Val Glu Ser Gly Ala Glu Val Lys Pro Gly Ala
1               5                   10                  15

Ser Val Lys Val Ser Cys Lys Ala Ser Gly Tyr Ser Phe Ser Asp Tyr
            20                  25                  30

Thr Met Asn Trp Val Arg Gln Ala Pro Gly Gln Arg Leu Glu Trp Ile
            35                  40                  45

Gly Leu Ile Asn Pro Tyr Asn Gly Gly Thr Ser Tyr Asn Gln Asn Phe
        50                  55                  60

Lys Gly Arg Val Thr Leu Thr Val Asp Thr Ser Ala Ser Thr Ala Tyr
65                  70                  75                  80

Leu Glu Leu Asn Ser Leu Arg Ser Glu Asp Thr Gly Val Tyr Tyr Cys
                85                  90                  95

Ala Arg Glu Asp Tyr Asp Gly Tyr Leu Tyr Phe Ala Met Asp Tyr Trp
                100                 105                 110

Gly Gln Gly Thr Leu Val Thr Val Ser Ser
            115                 120
```

<210> SEQ ID NO 13
<211> LENGTH: 122
<212> TYPE: PRT
<213> ORGANISM: Artificial Sequence
<220> FEATURE:
<223> OTHER INFORMATION: Synthetic sequence: Humanised VH domain

<400> SEQUENCE: 13

```
Glu Val Gln Leu Val Glu Ser Gly Ala Glu Val Lys Pro Gly Ala
1               5                   10                  15

Ser Val Lys Val Ser Cys Lys Ala Ser Gly Tyr Ser Phe Thr Asp Tyr
            20                  25                  30

Thr Met Asn Trp Val Arg Gln Ala Pro Gly Gln Arg Leu Glu Trp Ile
            35                  40                  45

Gly Leu Ile Asn Pro Tyr Asn Gly Gly Thr Ser Tyr Asn Gln Asn Phe
        50                  55                  60

Lys Gly Arg Val Thr Leu Thr Arg Asp Thr Ser Ala Ser Thr Ala Tyr
65                  70                  75                  80

Leu Glu Leu Asn Ser Leu Arg Ser Glu Asp Thr Gly Val Tyr Tyr Cys
                85                  90                  95

Ala Arg Glu Asp Tyr Asp Gly Tyr Leu Tyr Phe Ala Met Asp Tyr Trp
                100                 105                 110

Gly Gln Gly Thr Leu Val Thr Val Ser Ser
            115                 120
```

<210> SEQ ID NO 14
<211> LENGTH: 122
<212> TYPE: PRT
<213> ORGANISM: Artificial Sequence
<220> FEATURE:
<223> OTHER INFORMATION: Synthetic sequence: Humanised VH domain

<400> SEQUENCE: 14

```
Glu Val Gln Leu Val Glu Ser Gly Ala Glu Val Lys Pro Gly Ala
1               5                   10                  15

Ser Val Lys Val Ser Cys Lys Ala Ser Gly Tyr Ser Phe Thr Asp Tyr
            20                  25                  30

Thr Met Asn Trp Val Arg Gln Ala Pro Gly Gln Arg Leu Glu Trp Ile
            35                  40                  45

Gly Leu Ile Asn Pro Tyr Asn Gly Gly Thr Ser Tyr Asn Gln Asn Phe
        50                  55                  60
```

```
Lys Gly Arg Val Thr Leu Thr Val Asp Thr Ser Ala Ser Thr Ala Tyr
 65                  70                  75                  80

Leu Glu Leu Asn Ser Leu Arg Ser Glu Asp Thr Gly Val Tyr Tyr Cys
             85                  90                  95

Ala Arg Glu Asp Tyr Asp Gly Tyr Leu Tyr Phe Ala Met Asp Tyr Trp
         100                 105                 110

Gly Gln Gly Thr Leu Val Thr Val Ser Ser
        115                 120
```

<210> SEQ ID NO 15
<211> LENGTH: 107
<212> TYPE: PRT
<213> ORGANISM: Mus musculus

<400> SEQUENCE: 15

```
Asp Ile Gln Met Thr Gln Thr Thr Ser Ser Leu Ser Ala Ser Leu Gly
  1               5                  10                  15

Asp Arg Val Thr Ile Ser Cys Ser Ala Ser Gln Gly Ile Ser Asn Tyr
             20                  25                  30

Leu Asn Trp Tyr Gln Gln Lys Ala Asp Gly Thr Val Glu Leu Leu Ile
         35                  40                  45

Tyr Tyr Thr Ser Ser Leu His Ser Gly Val Pro Ser Arg Phe Ser Gly
 50                  55                  60

Ser Gly Ser Gly Thr Asp Tyr Ser Leu Thr Ile Ser Asn Leu Glu Pro
 65                  70                  75                  80

Glu Asp Ile Ala Thr Tyr Tyr Cys Gln Gln Tyr Ser Lys Leu Pro Tyr
             85                  90                  95

Thr Phe Gly Gly Gly Thr Lys Leu Glu Ile Lys
         100                 105
```

<210> SEQ ID NO 16
<211> LENGTH: 321
<212> TYPE: DNA
<213> ORGANISM: Mus musculus

<400> SEQUENCE: 16

```
gacatccaga tgacccagac cacctccagc ctgagcgcca gcctgggcga ccgggtgacc      60
atcagctgca gcgcctccca gggcatcagc aactacctga actggtatca gcagaaggcc     120
gacggcaccg tcgagctgct gatctactac accagcagcc tgcacagcgg cgtgcccagc     180
cggtttagcg gcagcggctc cggcaccgac tacagcctga ccatctccaa cctggaaccc     240
gaggatatcg ccacctacta ctgccagcag tacagcaagc tgccctacac ctttggcggc     300
ggaacaaagc tggaaatcaa g                                                321
```

<210> SEQ ID NO 17
<211> LENGTH: 139
<212> TYPE: PRT
<213> ORGANISM: Mus musculus

<400> SEQUENCE: 17

```
Met Val Leu Ser Leu Leu Tyr Leu Leu Thr Ala Leu Pro Gly Ile Leu
  1               5                  10                  15

Ser Glu Val Gln Leu Gln Gln Ser Gly Pro Glu Leu Val Lys Pro Gly
             20                  25                  30

Ala Ser Met Lys Ile Ser Cys Lys Ala Ser Gly Tyr Ser Phe Thr Asp
         35                  40                  45

Tyr Thr Met Asn Trp Val Lys Gln Ser His Gly Lys Asn Leu Glu Trp
 50                  55                  60
```

```
Ile Gly Leu Ile Asn Pro Tyr Asn Gly Thr Ser Tyr Asn Gln Asn
 65                  70                  75                  80

Phe Lys Gly Lys Ala Thr Leu Thr Val Asp Lys Ser Ser Thr Ala
                 85                  90                  95

Tyr Met Glu Leu Leu Ser Leu Thr Ser Glu Asp Ser Ala Val Tyr Tyr
            100                 105                 110

Cys Ala Arg Glu Gly Tyr Asp Gly Tyr Leu Tyr Phe Ala Met Asp Tyr
            115                 120                 125

Trp Gly Gln Gly Thr Ser Val Thr Val Ser Ser
        130                 135

<210> SEQ ID NO 18
<211> LENGTH: 417
<212> TYPE: DNA
<213> ORGANISM: Mus musculus

<400> SEQUENCE: 18
atggtgctgt ccctgctgta cctgctgacc gccctgcccg gcatcctgag cgaggtgcag      60
ctgcagcaga gcggccctga gctggtgaag cctggcgcca gcatgaagat cagctgcaag     120
gccagcggct acagcttcac cgactacacc atgaactggg tgaagcagag ccacggcaag     180
aacctggaat ggatcggcct gatcaacccc tacaacggcg gcaccagcta caaccagaac     240
ttcaagggca aggccaccct gaccgtggac aagagcagca gcaccgccta catggaactg     300
ctgtctctga ccagcgagga cagcgccgtg tactactgcg ccagagaggg ctacgacggc     360
tacctgtact tcgccatgga ctactggggc cagggcacca gcgtgaccgt gagcagc       417

<210> SEQ ID NO 19
<211> LENGTH: 137
<212> TYPE: PRT
<213> ORGANISM: Homo sapiens

<400> SEQUENCE: 19

Leu Leu Leu Ala Val Leu Gln Gly Val Cys Ala Glu Val Arg Leu Val
  1               5                  10                  15

Gln Ser Gly Ala Glu Val Lys Lys Pro Gly Glu Ser Leu Lys Ile Ser
                 20                  25                  30

Cys Lys Ala Ser Gly Tyr Ser Phe Thr Ser Asn Trp Ile Gly Trp Val
             35                  40                  45

Arg Gln Met Pro Gly Lys Gly Leu Glu Trp Ile Gly Ile Ile Phe Pro
         50                  55                  60

Gly Asp Ser Asp Thr Ile Tyr Ser Pro Ser Phe Gln Gly Gln Val Thr
 65                  70                  75                  80

Ile Ser Val Asp Lys Ser Ile Asn Thr Ala Tyr Leu Gln Trp Ser Ser
                 85                  90                  95

Leu Lys Ala Thr Asp Thr Ala Met Tyr Tyr Cys Ala Arg Gln Asn Pro
            100                 105                 110

Pro Glu Tyr Ser Gly Ala Tyr His Asp Gly Trp Phe Asp Pro Trp Gly
            115                 120                 125

Gln Gly Thr Leu Val Ile Val Ser Ser
        130                 135

<210> SEQ ID NO 20
<211> LENGTH: 411
<212> TYPE: DNA
<213> ORGANISM: Homo sapiens

<400> SEQUENCE: 20
```

```
ctcctcctgg ctgttctcca aggagtctgt gccgaggtgc gccttgtgca gtctggagca    60
gaggtgaaaa agccggggga gtctctgaag atctcctgta aggcttctgg atacagtttt   120
accagtaact ggatcggctg ggtgcgccag atgcccggga aaggcctgga gtggattggg   180
atcatctttc ctggtgactc tgataccata tacagcccgt ccttccaagg ccaggtcacc   240
atttcagtcg acaagtccat caataccgcc tacctgcagt ggagcagcct gaaggccacg   300
gacaccgcca tgtattactg tgcgagacag aaccccccg agtatagtgg cgcatatcat   360
gatgggtggt tcgacccctg gggccaggga accctggtca tcgtctcctc a            411
```

<210> SEQ ID NO 21
<211> LENGTH: 141
<212> TYPE: PRT
<213> ORGANISM: Artificial Sequence
<220> FEATURE:
<223> OTHER INFORMATION: Synthetic sequence: RHA VH domain

<400> SEQUENCE: 21

```
Met Gly Ser Thr Ala Ile Leu Gly Leu Leu Leu Ala Val Leu Gln Gly
 1               5                  10                  15

Val Cys Ala Glu Val Arg Leu Val Gln Ser Gly Ala Glu Val Lys Lys
             20                  25                  30

Pro Gly Glu Ser Leu Lys Ile Ser Cys Lys Ala Ser Gly Tyr Ser Phe
         35                  40                  45

Thr Asp Tyr Thr Met Asn Trp Val Arg Gln Met Pro Gly Lys Gly Leu
     50                  55                  60

Glu Trp Ile Gly Leu Ile Asn Pro Tyr Asn Gly Gly Thr Ser Tyr Asn
 65                  70                  75                  80

Gln Asn Phe Lys Gly Gln Val Thr Ile Ser Val Asp Lys Ser Ile Asn
                 85                  90                  95

Thr Ala Tyr Leu Gln Trp Ser Ser Leu Lys Ala Thr Asp Thr Ala Met
            100                 105                 110

Tyr Tyr Cys Ala Arg Glu Gly Tyr Asp Gly Tyr Leu Tyr Phe Ala Met
        115                 120                 125

Asp Tyr Trp Gly Gln Gly Thr Leu Val Ile Val Ser Ser
    130                 135                 140
```

<210> SEQ ID NO 22
<211> LENGTH: 424
<212> TYPE: DNA
<213> ORGANISM: Artificial Sequence
<220> FEATURE:
<223> OTHER INFORMATION: Synthetic sequence: Nucleic acid encoding RHA
      VH domain

<400> SEQUENCE: 22

```
atggggtcaa ccgccatcct tggcctcctc ctggctgttc tccaaggagt ctgtgccgaa    60
gtgcgccttg tgcagtctgg agcagaagtg aaaaagccgg gggagtctct gaagatctct   120
tgcaaggctt ctggatacag ttttaccgac tacaccatga actgggtgcg ccagatgccc   180
gggaaaggcc tggagtggat tggcttatta atccttacaa tggtggtac tagctacaac   240 cagaatttca aggccaagt caccatttca gtcgacaagt ccatcaatac cgcctacctg   300
cagtggagca gcctgaaggc cacggacacc gccatgtatt actgtgcgag agagggctat   360
gatggttacc tttactttgc tatggactac tggggccagg aaccctggt catcgtctcc   420 tcag                                                                424
```

<210> SEQ ID NO 23
<211> LENGTH: 127
<212> TYPE: PRT
<213> ORGANISM: Homo sapiens

<400> SEQUENCE: 23

Met Arg Val Pro Ala Gln Leu Leu Gly Leu Leu Leu Leu Trp Leu Pro
1               5                   10                  15

Asp Thr Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Ser Asn Tyr Leu Ala Trp Tyr Gln Gln Lys Pro Gly Lys Val Pro
    50                  55                  60

Lys Leu Leu Ile Tyr Ala Ala Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Tyr Cys Gln Lys Tyr Asn
            100                 105                 110

Ser Ala Pro Tyr Thr Phe Gly Gln Gly Thr Lys Leu Glu Ile Lys
        115                 120                 125

<210> SEQ ID NO 24
<211> LENGTH: 381
<212> TYPE: DNA
<213> ORGANISM: Homo sapiens

<400> SEQUENCE: 24
atgagggtcc ctgctcagct cctgggactc ctgctgctct ggctcccaga taccagatgt      60
gacatccaga tgacccagtc tccatcctcc ctgtctgcat ctgtaggaga cagagtcacc     120
atcacttgcc gggcgagtca gggcattagc aattatttag cctggtatca gcagaaacca     180
gggaaagttc ctaaactcct gatctatgct gcatccactt tgcaatcagg ggtcccatct     240
cggttcagcg gcagtggatc tgggacagat ttcactctca ccatcagcag cctgcagcct     300
gaagatgttg caacttatta ctgtcaaaag tataacagtg ccccgtacac ttttggccag     360
gggaccaagc tggagatcaa a                                               381

<210> SEQ ID NO 25
<211> LENGTH: 127
<212> TYPE: PRT
<213> ORGANISM: Artificial Sequence
<220> FEATURE:
<223> OTHER INFORMATION: Synthetic sequence: Humanised 2c3 VK domain RKA

<400> SEQUENCE: 25

Met Arg Val Pro Ala Gln Leu Leu Gly Leu Leu Leu Leu Trp Leu Pro
1               5                   10                  15

Asp Thr Arg Cys Asp Ile Gln Met Thr Gln Ser Pro Ser Ser Leu Ser
            20                  25                  30

Ala Ser Val Gly Asp Arg Val Thr Ile Thr Cys Ser Ala Ser Gln Gly
        35                  40                  45

Ile Ser Asn Tyr Leu Asn Trp Tyr Gln Gln Lys Pro Gly Lys Val Pro
    50                  55                  60

Lys Leu Leu Ile Tyr Tyr Thr Ser Ser Leu His Ser Gly Val Pro Ser
65                  70                  75                  80

Arg Phe Ser Gly Ser Gly Ser Gly Thr Asp Phe Thr Leu Thr Ile Ser
                85                  90                  95

```
Ser Leu Gln Pro Glu Asp Val Ala Thr Tyr Tyr Cys Gln Gln Tyr Ser
                100                 105                 110

Lys Leu Pro Tyr Thr Phe Gly Gln Gly Thr Lys Leu Glu Ile Lys
        115                 120                 125

<210> SEQ ID NO 26
<211> LENGTH: 381
<212> TYPE: DNA
<213> ORGANISM: Artificial Sequence
<220> FEATURE:
<223> OTHER INFORMATION: Synthetic sequence: Nucleic acid encoding
      humanised 2c3 VK domain RKA

<400> SEQUENCE: 26
atgagggtcc ctgctcagct cctgggactc ctgctgctct ggctcccaga taccagatgt      60
gacatccaga tgacccagtc tccatcctcc ctgtctgcat ctgtaggaga cagagtcacc     120
atcacttgca gtcatcccca gggcattagc aattatctga attggtatca gcagaaacca     180
gggaaagttc ctaaactcct gatctattac acatcaagtt acactcagg ggtcccatct      240 cggttcagcg gcagtggatc tgggacagat ttcactctca ccatcagcag cctgcagcct     300
gaagatgttg caacttatta ctgtcagcag tatagcaagc tgccgtacac gtttggccag     360
gggaccaagc tggagatcaa a                                                381

<210> SEQ ID NO 27
<211> LENGTH: 121
<212> TYPE: PRT
<213> ORGANISM: Homo sapiens

<400> SEQUENCE: 27

Glu Val Gln Leu Val Glu Ser Gly Ala Glu Val Lys Lys Pro Gly Ala
  1               5                  10                  15

Ser Val Lys Val Ser Cys Lys Ala Ser Gly Tyr Ser Phe Ser Ser Tyr
             20                  25                  30

Gly Ile His Trp Val Arg Gln Ala Pro Gly Gln Arg Leu Glu Trp Met
         35                  40                  45

Gly Trp Ile Asn Gly Gly Thr Gly Phe Thr Lys Tyr Ser Gln Asn Phe
     50                  55                  60

Gln Gly Arg Val Thr Leu Thr Arg Asp Thr Ser Ala Ser Thr Ala Tyr
 65                  70                  75                  80

Leu Glu Leu Asn Ser Leu Arg Ser Glu Asp Thr Gly Val Tyr Tyr Cys
                 85                  90                  95

Ala Arg Asp Pro Tyr Asn Asn Tyr Ala Ala Glu Leu Asp Tyr Trp Gly
            100                 105                 110

Gln Gly Thr Leu Val Thr Val Ser Ser
        115                 120

<210> SEQ ID NO 28
<211> LENGTH: 363
<212> TYPE: DNA
<213> ORGANISM: Homo sapiens

<400> SEQUENCE: 28
gaggtgcagc tggtggagtc tggggctgag gtgaagaagc ctggggcctc agtgaaagtt      60
tcgtgcaagg cttctggata tcccttcagt agttatggta cattgggt gcgccaggcc       120 cccggacaaa ggcttgagtg gatgggatgg atcaacggtg gcactggttt tacaaaatat     180
tcacagaatt tcagggcag agtcacccta accagggaca cttccgcgag cacagcctac      240
```

```
ttggaactga acagcctgag atctgaagac acgggtgtat attactgtgc gagggatccc    300
tacaataact acgcggcgga acttgactac tggggccagg gaaccctggt caccgtctcc    360
tca                                                                  363
```

<210> SEQ ID NO 29
<211> LENGTH: 11
<212> TYPE: PRT
<213> ORGANISM: Mus musculus
<400> SEQUENCE: 29

Ser Ala Ser Gln Gly Ile Ser Asn Tyr Leu Asn
1               5                   10

<210> SEQ ID NO 30
<211> LENGTH: 7
<212> TYPE: PRT
<213> ORGANISM: Mus musculus
<400> SEQUENCE: 30

Tyr Thr Ser Ser Leu His Ser
1               5

<210> SEQ ID NO 31
<211> LENGTH: 9
<212> TYPE: PRT
<213> ORGANISM: Mus musculus
<400> SEQUENCE: 31

Gln Gln Tyr Ser Lys Leu Pro Tyr Thr
1               5

<210> SEQ ID NO 32
<211> LENGTH: 5
<212> TYPE: PRT
<213> ORGANISM: Mus musculus
<400> SEQUENCE: 32

Asp Tyr Thr Met Asn
1               5

<210> SEQ ID NO 33
<211> LENGTH: 13
<212> TYPE: PRT
<213> ORGANISM: Mus musculus
<400> SEQUENCE: 33

Glu Gly Tyr Asp Gly Tyr Leu Tyr Phe Ala Met Asp Tyr
1               5                   10

<210> SEQ ID NO 34
<211> LENGTH: 5
<212> TYPE: PRT
<213> ORGANISM: Artificial Sequence
<220> FEATURE:
<223> OTHER INFORMATION: Synthetic sequence: Heavy Chain CDR1

<400> SEQUENCE: 34

Gly Tyr Thr Met Asn
1               5

<210> SEQ ID NO 35
<211> LENGTH: 17
<212> TYPE: PRT
<213> ORGANISM: mus musculus

```
<400> SEQUENCE: 35

Leu Ile Asn Pro Tyr Asn Gly Gly Thr Ser Tyr Asn Gln Asn Phe Lys
1               5                   10                  15
Gly

<210> SEQ ID NO 36
<211> LENGTH: 13
<212> TYPE: PRT
<213> ORGANISM: Artificial Sequence
<220> FEATURE:
<223> OTHER INFORMATION: Synthetic sequence: Heavy Chain CDR3

<400> SEQUENCE: 36

Glu Asp Tyr Asp Gly Tyr Leu Tyr Phe Ala Met Asp Tyr
1               5                   10

<210> SEQ ID NO 37
<211> LENGTH: 19
<212> TYPE: PRT
<213> ORGANISM: Homo sapiens

<400> SEQUENCE: 37

Met Gly Ser Thr Ala Ile Leu Gly Leu Leu Leu Ala Val Leu Gln Gly
1               5                   10                  15
Val Cys Ala

<210> SEQ ID NO 38
<211> LENGTH: 20
<212> TYPE: PRT
<213> ORGANISM: Mus musculus

<400> SEQUENCE: 38

Met Arg Val Pro Ala Gln Leu Leu Gly Leu Leu Leu Leu Trp Leu Pro
1               5                   10                  15
Asp Thr Arg Cys
            20

<210> SEQ ID NO 39
<211> LENGTH: 22
<212> TYPE: PRT
<213> ORGANISM: Homo sapiens

<400> SEQUENCE: 39

Met Asp Met Arg Val Pro Ala Gln Leu Leu Gly Leu Leu Leu Leu Trp
1               5                   10                  15
Leu Pro Asp Thr Arg Cys
            20

<210> SEQ ID NO 40
<211> LENGTH: 423
<212> TYPE: DNA
<213> ORGANISM: Artificial Sequence
<220> FEATURE:
<223> OTHER INFORMATION: Synthetic sequence: Nucleic acid encoding RH2.5
      R71V

<400> SEQUENCE: 40
atgggcagca cagccattct gggcctgctg ctggccgtgc tgcagggcgt gtgcgccgag     60
gtgcagctgg tcgagagcgg agccgaggtg aagaagccag cgccagcgt caaggtgtcc    120 tgcaaggcca gcggctacag cttctccggc tacaccatga actgggtgcg gcaggcccca    180
ggccagaggc tggaatggat gggcctgatc aaccccctaca acggcggcac cagctacaac    240
```

```
cagaacttca agggcagggt gacactgacc gtggatacca gcgccagcac cgcctacctg    300
gaactgaaca gcctgagaag cgaggacacc ggcgtgtact actgcgccag agaggactac    360
gacggctacc tgtacttcgc catggactac tggggccagg gcaccctggt gaccgtgagc    420
agc                                                                  423

<210> SEQ ID NO 41
<211> LENGTH: 15
<212> TYPE: DNA
<213> ORGANISM: Artificial Sequence
<220> FEATURE:
<223> OTHER INFORMATION: Synthetic sequence: Kozak consensus sequence

<400> SEQUENCE: 41
aagcttgccg ccacc                                                     15
```

ANTIBODIES AGAINST IL-25

RELATED APPLICATIONS

This application is the U.S. National Stage of International Application No. PCT/IB2009/007302, filed on Sep. 30, 2009, which designates the U.S., published in English, which claims the benefit of U.S. Provisional Application No. 61/101,293, filed on Sep. 30, 2008, and claims priority under 35 U.S.C. §119 or 365 to Great Britain Application No. GB 0817891.5, filed Sep. 30, 2008. The entire teachings of the above applications are incorporated herein by reference.

FIELD OF THE INVENTION

The present invention relates to antibodies, including binding fragments thereof, directed to interleukin 25 (IL-25).

INCORPORATION BY REFERENCE OF MATERIAL IN ASCII TEXT FILE

This application incorporates by reference the Sequence Listing contained in the following file:
a) File name: 44331001003 SubSeqListing.txt; created Jan. 10, 2013, 32 KB in size.

BACKGROUND OF THE INVENTION

Asthma

Asthma is a common chronic inflammatory disorder of the airways. The number of sufferers has increased dramatically over recent decades and the World Health Organisation estimates that in the region of 300 million people worldwide suffer from asthma. Allergic asthma is characterised by uncontrollable airways hyperresponsiveness (AHR) induced by a variety of provocative stimuli and is associated with type-2 inflammatory infiltrates into the lungs.

Type-2 cytokines play an important role in mediating protective immunity to parasitic helminth infection, regulating effector functions such as B cell growth and IgE secretion, inducing goblet cell hyperplasia and associated mucus production, eosinophilia, mastocytosis and fibrosis (1). It is the central roles played by these cytokines in the regulation of these effector functions that have made them key therapeutic targets in asthma. Indeed, mouse models in which these cytokines are over-expressed show significant characteristics of asthma. Surprisingly then, efforts to ameliorate experimental asthma by blocking specific type-2 cytokines have, with the exception of inhibiting IL-13, proven unsuccessful.

Inhibition of IL-13 suppresses both AHR and airway inflammation although the mechanism remains unclear (2, 3). However, given the complex pathophysiology and poorly understood etiology of asthma, it is uncertain whether targeting individual pathways will ultimately prove successful therapeutically.

Recently, over-expression of IL-25/IL-17E, a member of the structurally related IL-17 cytokine family (8), has been shown to induce type-2 responses in vivo (4-6) and increase responsiveness to airway agonists (7). Il25$^{-/-}$ mice failed to expel helminth parasites efficiently; a key indicator of an ineffectual type-2 response (9, 10) IL-25 has also been shown to be upregulated in samples from patients with asthma.

Inflammatory Bowel Disease

Inflammatory bowel disease (IBD) is a chronic inflammation affecting the mucosal layer of the large intestine or colon, which typically comprises one or more disease conditions selected from the group consisting of ulcerative colitis (UC) and Crohn's disease (CD). UC is thought to be a Th2-mediated disease, with a representative mouse model showing involvement of type 2 cytokines in the development of gut inflammation (16). IL-25 production has been observed in a mouse model of chronic colitis, in association with a switch from a Th1 to a Th2 type response (17) and high expression of IL-25 mRNA has been reported throughout the gastrointestinal tract in mice (18). Moreover the IL-25 gene is located within a Crohn's disease susceptibility region on chromosome 14, although its potential association with the disease remains to be investigated (19). In addition, IBD can comprise one or more disease conditions selected from the group consisting of collagenous colitis, lymphocytic colitis, ischemic colitis, diversion colitis, Behçet's syndrome, infective colitis and indeterminate colitis.

Conventional therapies for treatment of IBD involve either antibiotics or steroid-derived drugs; however these are not currently successful in inducing or maintaining clinical remission in patients (20). A therapy involving anti-TNF-α agents is also currently available, despite showing poor efficacy (21, 22). This shows that there is a clear need for new and more effective therapies in the treatment of inflammatory bowel diseases.

Antibodies

The basic structure of an antibody is well known in the art. A naturally-occurring antibody usually has four polypeptide chains: two identical heavy chains and two identical light chains connected by disulphide bonds. The heavy (VH) and light (VL) chains each have a constant region and a variable region (or domain). The variable regions are primarily responsible for antigen binding. Within each variable region, three subregions, known as the complementarity-determining regions (CDRs), make contact with the antigen. The CDRs of each variable domain are numbered, from the N-terminal to the C-terminal, as CDR1, CDR2 and CDR3. Between and N- and C-terminal to the CDRs are four so-called framework regions, which make few if any contacts with the antigen. More details regarding the structures of antibodies are illustrated in many of the documents cited below, which are incorporated herein by reference.

There are a number of ways in which antibodies against a target antigen may be raised. The generation of monoclonal antibodies using hybridoma technology is one such method. Antibodies are usually generated in mice or other rodents. This can be a useful way to generate high-affinity antibodies. However, for such antibodies to then be useful in human therapy, it is usually necessary to transfer the CDRs of the antibodies into a human framework. This is to try to avoid a human-anti-mouse-antibody response in a patient.

The general principle of CDR-grafting was described by Jones et al and Riechman et al (11, 12). That is, the CDRs of a mouse antibody are transplanted into the framework regions of a recipient human antibody. In practice, though the resulting antibody will bind to the same target antigen as the original donor mouse antibody, the affinity of the grafted antibody is usually much reduced.

In addition, the thermostability of grafted antibodies can often be compromised.

Various ways to try to recover and optimise the properties of the original antibody are known in the art. For example, within the framework regions there are certain "canonical structure" residues Chothia & Lesk (13) that are associated with certain germline CDRs. Further, Foote & Winter (14) have identified "Vernier zone" residues (some of which are also canonical structure residues) that support antigen-binding loop conformations and their relative dispositions and has therefore been suggested to play an important role in fine-tuning the fit of an antibody to antigen. In addition, further residues within the framework are believed to stabilize and maintain the VH/VL interface. Accordingly, those of skill in the art looking to humanise an antibody often look for human frameworks in which the Vernier zone, Canonical and Interface ("VCI") residues correspond as closely as possible to those of the original donor antibody.

However each antibody represents a unique challenge to those of skill in the art and there is no certainty that any generally known methodology for CDR grafting is directly applicable in each case.

The present inventors and colleagues (Ballantyne et al (15)) report the production of a mouse monoclonal antibody, 2C3, that binds to IL-25 and in vivo is able to block airway hyperresponsiveness in allergic asthma. To date, the sequence of the antibody is not available to the public.

PCT/GB2008/001365, published on 30 Oct. 2008 as WO2008/129263, reports the sequence of the 2C3 antibody and its use in blocking airway hyper-responsiveness.

DISCLOSURE OF THE INVENTION

The present invention relates to a humanised (CDR-grafted) antibody that is based upon the 2C3 sequence. In producing this antibody, a number of challenges had to be overcome.

The inventors first of all selected a recipient human antibody VH chain with maximum VCI homology, namely 20 of the 22 VCI residues. However, it was found that the resulting antibody ("RHA") bound to IL-25 to a significantly less extent than 2C3 itself. Despite a number of further modifications to the antibody, including changes to the VCI designated amino acids and residues that appeared to represent rare somatic mutations, little improvement to antibody binding was achieved.

In an attempt to overcome the failure of the VCI homology approach to antibody humanisation, a different human VH framework with a lower VCI residue match (17/22) but very slightly higher overall homology was selected. The resulting antibody provided higher binding than the "RHA" antibody, though this was still not as great as the parent 2C3 antibody.

In order to maximise binding and minimise non-human residues that risk provoking an antibody response, further framework and CDR changes were made. The resulting antibody was found to have enhanced binding compared to 2C3 and in an in vivo test of inhibition of airway-hyperresponsiveness was found to be significantly more potent than 2C3. The antibody also exhibited good thermostability.

The present invention relates the humanised VH chain derived from 2C3. In some aspects, the invention relates to an antibody comprising this chain. The antibody may comprise a humanised VL chain comprising the 2C3 VL CDRs.

Thus in one aspect, the invention provides an antibody VH domain which comprises SEQ ID NO:1:

Glu Val Gln Leu Val Glu Ser Gly Ala Glu Val Lys

Lys Pro Gly Ala Ser Val Lys Val Ser Cys Lys Ala

Ser Gly Tyr Ser Phe Xa1 Xa2 Tyr Thr Met Asn Trp

Val Arg Gln Ala Pro Gly Gln Arg Leu Glu Trp Xa3

Gly Leu Ile Asn Pro Tyr Asn Gly Gly Thr Ser Tyr

Asn Gln Asn Phe Lys Gly Arg Val Thr Leu Thr Xa4

Asp Thr Ser Ala Ser Thr Ala Tyr Leu Glu Leu Asn

Ser Leu Arg Ser Glu Asp Thr Gly Val Tyr Tyr Cys

Ala Arg Glu Xa5 Tyr Asp Gly Tyr Leu Tyr Phe Ala

Met Asp Tyr Trp Gly Gln Gly Thr Leu Val Thr Val

Ser Ser wherein:
Xa1 is Ser or Thr;
Xa2 is Gly, Asp, Ala, Ser, Val, Asn, Lys, Tyr or Met;
Xa3 is Met or Ile;
Xa4 is Val or Arg; and
Xa5 is Asp, Asn or Gly.

In one aspect, the residues Xa1-Xa5 may be selected from the following combinations:
Xa1 is Ser or Thr;
Xa2 is Gly or Asp;
Xa3 is Met or Ile;
Xa4 is Val or Arg; and
Xa5 is Asp, Asn or Gly.

In some embodiments, Xa2 is Gly and Xa5 is Asp or Asn, preferably Asp.

In some embodiments (including those where Xa2 is Gly and Xa5 is Asp or Asn, preferably Asp), Xa1 is Ser.

In some embodiments (including those where Xa2 is Gly and Xa5 is Asp or Asn, preferably Asp), Xa1 is Thr.

In some embodiments, including all the above-described combinations of Xa2, Xa5 and Xa1, Xa3 is Met.

In some embodiments, including all the above-described combinations of Xa2, Xa5 and Xa1, Xa3 is Ile.

All the above-described embodiments may be combined with either of the values of Xa4, i.e. Val or Arg.

Particular combinations of the above residues are set out in the table below. For the convenience of the skilled reader and for consistency with the accompanying examples, the table lists the Kabat numbering of the residues. In some cases, this differs from the numbering of the sequence listing.

| Kabat Res: | 30 | 31 | 48 | 71 | 96 |
|---|---|---|---|---|---|
| Position in SEQ ID NO: 1: | 30 | 31 | 48 | 72 | 100 |
| Seq List Res: | Xa1 | Xa2 | Xa3 | Xa4 | Xa5 |
| SEQ ID NO: 2 | Ser | Gly | Met | Val | Asp |
| SEQ ID NO: 3 | Thr | Gly | Met | Arg | Asp |
| SEQ ID NO: 4 | Ser | Gly | Met | Arg | Asp |
| SEQ ID NO: 5 | Thr | Gly | Met | Val | Asp |
| SEQ ID NO: 6 | Ser | Asp | Met | Val | Asp |
| SEQ ID NO: 7 | Thr | Asp | Met | Arg | Asp |
| SEQ ID NO: 8 | Thr | Asp | Met | Val | Asp |
| SEQ ID NO: 9 | Ser | Gly | Ile | Val | Asp |
| SEQ ID NO: 10 | Thr | Gly | Ile | Arg | Asp |
| SEQ ID NO: 11 | Thr | Gly | Ile | Val | Asp |
| SEQ ID NO: 12 | Ser | Asp | Ile | Val | Asp |
| SEQ ID NO: 13 | Thr | Asp | Ile | Arg | Asp |
| SEQ ID NO: 14 | Thr | Asp | Ile | Val | Asp |

The VH domain may be combined with a light chain variable domain to provide a specific target binding member that binds IL-25.

A suitable light chain domain is one that comprises the CDR residues of the 2C3 antibody. Preferably the light chain is a humanised light chain, i.e. comprises human framework sequences and the CDR regions of 2C3. The light chain domain of 2C3 is shown as SEQ ID NO:15. The CDR regions 1-3 may comprise residues 30-34, for example, may comprise residues 24-34 (SEQ ID NO:29); 50-56 (SEQ ID NO:30) and 89-97 (SEQ ID NO:31) respectively.

The CDR residues may be in the native 2C3 antibody light chain or may be transferred into a humanised light chain molecule.

The residues 35-38, though not comprising the CDR, are highly conserved between mouse and human light chain sequences and may also be transferred.

An example of a humanised VL chain comprises residues 21-127 SEQ ID NO:25. However, other human frameworks which comprise the three CDR regions of SEQ ID NO:15 may also be used. Further, as indicated below, antibody leader sequences other than the non-native antibody leader sequence of a VL chain may be used. Thus in one embodiment the VL chain comprises SEQ ID NO:25. In another embodiment the VL chain may comprise an antibody leader sequence such as one described herein below fused to residues 21-127 of SEQ ID NO:25.

The invention further provides the use of target binding members of the invention, for example in the form of a pharmaceutical composition, for the treatment of diseases, including inflammatory conditions such as asthma (including allergic asthma), Crohn's disease and ulcerative colitis.

These and further aspects of the invention are described in further detail below and with reference to the accompanying examples.

BRIEF DESCRIPTION OF THE DRAWINGS

FIG. 1 shows the kappa light chain nucleotide (SEQ ID NO:16) and amino acid (SEQ ID NO:15) sequence of 2c3 mouse antibody. Shading denotes the CDRs.

FIG. 2 shows the heavy chain nucleotide (SEQ ID NO:18) and amino acid (SEQ ID NO:17) sequence of 2c3 mouse antibody. Shading denotes the CDRs.

FIG. 3 shows the DNA (SEQ ID NO:20) and amino acid (SEQ ID NO:19) sequence of AY393094.

FIG. 4 shows the DNA (SEQ ID NO:22) and amino acid (SEQ ID NO:21) sequence of humanised 2c3 RHA.

FIG. 5 shows the DNA (SEQ ID NO:24) and amino acid (SEQ ID NO:23) sequence of AY510106

FIG. 6 shows the DNA (SEQ ID NO:26) and amino acid (SEQ ID NO:25) sequence of the humanised kappa light chain 2c3 RKA.

FIGS. 7A-C show a comparison of binding activity of humanised antibody 2c3 RHA/RKA and variants with chimeric 2c3.

FIG. 8 shows the DNA (SEQ ID NO:28) and amino acid (SEQ ID NO:27) sequence of the framework AJ399823 used in the design of humanised 2c3-RH2.

FIGS. 9A and B show the effect of specific CDR mutations to 2c3 RH2bcdef binding to IL-25.

FIG. 10 shows the effect on IL-25 binding by combining CDR mutations D31G and G96D.

FIG. 11 shows comparison of 2c3 RH2.5_S30T and 2c3 RH2.5_R71V binding to IL-25

FIG. 12 is the protocol for in vivo mouse model of AHR.

FIGS. 13A and B show the effect of administering 2c3 RH2.5_R71V on pulmonary resistance in response to methacholine.

FIGS. 14A and B show colon length and body weight of mice in a model of colitis.

DETAILED DESCRIPTION OF THE INVENTION

Target Binding Member

This describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen antibody, biotin avidin, hormone hormone receptor, receptor-ligand, and enzyme substrate.

This application is concerned with antigen antibody type reactions. Accordingly, a target binding member of the invention will comprise at least a portion of an antibody molecule, more particularly at least part of the antigen-binding domain of such a molecule.

In general, the heavy chain variable region (VH domain) of an antibody plays a significant role in the binding of an antibody to an antigen. Thus target binding members of the invention are thus based around the those that comprise the VH domain that includes SEQ ID NO:1.

In making the VH domains of the present invention, it was found that the 2C3 antibody CDR regions were improved by altering the CDR1 and CDR3 sequences. Accordingly although preferred embodiments of the invention described herein contemplate VH domains of SEQ ID NO:1 in which Xa2 is Gly and Xa5 is Asp, the invention also contemplates humanised VH domains having human framework regions carrying the CDR1-3 regions of SEQ ID NO:34, SEQ ID NO:35 and SEQ ID NO:36 respectively.

Thus in further aspects the invention provides a target-binding member that binds IL-25 wherein the H1 heavy chain complementarity determining region (CDR) has an amino acid sequence of SEQ ID NO:34. In another aspect, the invention provides a target-binding member that binds IL-25 wherein the H2 heavy chain complementarity determining region (CDR) has an amino acid sequence of SEQ ID NO:35. In another aspect, the invention provides a target-binding member that binds IL-25 wherein the H3 heavy chain complementarity determining region (CDR) has an amino acid sequence of SEQ ID NO:36.

In a further aspect, the invention provides a target-binding member that binds IL-25 wherein the L1 light chain complementarity determining region (CDR) has an amino acid sequence of SEQ ID NO:29. In another aspect, the invention provides a target-binding member that binds IL-25 wherein the L2 light chain complementarity determining region (CDR) has an amino acid sequence of SEQ ID NO:30. In another aspect, the invention provides a target-binding member that binds IL-25 wherein the L3 light chain complementarity determining region (CDR) has an amino acid sequence of SEQ ID NO:31.

In a further aspect, the invention provides a target-binding member that binds IL-25 wherein the H1 heavy chain complementarity determining region (CDR) has an amino acid sequence of SEQ ID NO:34, the H2 heavy chain CDR has an amino acid sequence of SEQ ID NO:35 and the H3 heavy chain CDR has an amino acid sequence of SEQ ID NO:36. In one embodiment, such a target binding member has a L1 light chain CDR with an amino acid sequence of SEQ ID NO:29, a L2 light chain CDR of SEQ ID NO:30 and a L3 light chain CDR of SEQ ID NO:31.

The framework of such target-binding members may be human only, murine only or in accordance with the present invention, a framework which is primarily human but that retains one or more murine residues so as to enhance binding affinity.

Target binding members comprising said CDRs thus form a further aspect of the invention and may be used as described herein for target binding members with a VH domain comprising SEQ ID NO:1.

Generally, a target binding member comprises a VH domain paired with a VL domain to provide an antibody antigen binding domain. In one embodiment, the VH domain is paired with a VL domain whose CDRs, and optionally any framework residues conserved between human and mouse, are that from the 2C3 antibody.

However, light-chain promiscuity is well established in the art, as discussed further herein, and thus the VH may be paired with a VL domain other than the 2C3-derived VL. Such a VL may be selected as discussed herein below.

The structures and locations of immunoglobulin variable domains may be determined by reference to Kabat, E. A. et al, Sequences of Proteins of Immunological Interest. 4th Edition. US Department of Health and Human Services. 1987, and updates thereof. A number of academic and commercial on-line resources are available to query this database. For example, see Martin, A. C. R. Accessing the Kabat Antibody Sequence Database by Computer PROTEINS: Structure, Function and Genetics, 25 (1996), 130-133 and the associated on-line resource, currently at the web address of http://www.bioinforg.uk/abs/simkab.html.

A target binding member according to the present invention may bind IL-25 with an affinity substantially similar to that of the RHA2.5 R71V antibody described below, e.g. +10%. A target binding member will generally be specific for IL-25. Thus the target binding member will not show any significant binding to molecules other than its specific binding partner(s). For example, it has been found that the 2C3 antibody from which antibodies of the invention are derived does not cross-react with IL-4, IL-5 and IL-13 and thus avoidance of such cross-reactivity to other cytokines implicated in asthma and similar processes is a desirable feature of target binding members of the invention.

Typically, specificity may be determined by means of a binding assay such as ELISA employing a panel of antigens. A target binding member according to the present invention may recognise IL-25 and not other members of the IL-17 family, particular any one of IL-17A, IL-17B and IL-17C; more preferably all three of IL-17A, IL-17B and IL-17C. Binding of a target binding member according to the invention with IL-25 may be abolished by competition with recombinant IL-25.

Binding affinity and neutralisation potency of different target binding members can be compared under appropriate conditions.

Antibody Molecule

This describes an immunoglobulin whether natural or partly or wholly synthetically produced. It has been shown that fragments of a whole antibody can perform the function of binding antigens. Thus reference to an antibody also covers any polypeptide or protein comprising an antibody binding fragment.

Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) F(ab')2 fragments, a bivalent fragment comprising two linked Fab fragments (vi) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (vii) bispecific single chain Fv dimers (PCT/US92/09965) and (viii) "diabodies", multivalent or multispecific fragments constructed by gene fusion (WO94/13804; P. Holliger et al, Proc. Natl. Acad. Sci. USA 90 6444-6448, 1993). Fv, scFv or diabody molecules may be stabilised by the incorporation of disulphide bridges linking the VH and VL domains (Y. Reiter et al, Nature Biotech, 14, 1239-1245, 1996). Minibodies comprising a scFv joined to a CH3 domain may also be made (S. Hu et al, Cancer Res., 56, 3055-3061, 1996).

Where bispecific antibodies are to be used, these may be conventional bispecific antibodies, which can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against IL-25, then a library can be made where the other arm is varied and an antibody of appropriate specificity selected. Bispecific whole antibodies may be made by knobs-into-holes engineering (J. B. B. Ridgeway et al, Protein Eng., 9, 616-621, 1996).

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400.

Preferably the CDR regions of the VL chain of 2C3 are grafted into a human framework region. The human framework region may be selected by a number of methods, e.g. by comparing the mouse framework region or mouse VL region sequences with known human framework or VL region sequences and selecting a human framework region which has the highest, or one of the highest degrees of amino acid similarity or identity. Modifications to framework regions of native human sequences may be made in order to further optimize the resulting CDR-grafted antibodies.

Although in a preferred aspect of the invention antibody molecules comprising a pair of VH and VL domains are preferred, single binding domains based on either VH or VL domain sequences form further aspects of the invention. It is known that single immunoglobulin domains, especially VH domains, are capable of binding target antigens in a specific manner.

In the case of either of the single chain binding domains, these domains may be used to screen for complementary domains capable of forming a two-domain target binding member able to bind IL 25, as discussed further herein below.

Antibody molecules of the present invention may further comprise antibody constant regions or parts thereof. For example, a VL domain may be attached at its C-terminal end to antibody light chain constant domains including human Cκ or Cλ chains, preferably Cκ chains. Similarly, a target binding member based on a VH domain may be attached at its C-terminal end to all or part of an immunoglobulin heavy chain derived from any antibody isotype, e.g. IgG, IgA, IgE and IgM and any of the isotype sub-classes, particularly IgG1 and IgG4. IgG4 is preferred. Fc regions such as Δnab and Δnac as disclosed in WO99/58572 may be employed.

Chimeric molecules comprising an target binding domain, or equivalent, fused to another polypeptide are therefore included. Cloning and expression of chimeric antibodies are described in EP-A-0120694 and EP-A-0125023.

Framework regions of antibody molecules of the invention may also include glycosylation sequences that include one or more glycosylation sites. Depending upon the host cell in which the target binding member is expressed, the pattern of glycosylation may vary. Thus nucleic acid constructs that encode glycosylation sites may be modified to remove the site or alternatively such sites may be introduced into the protein. For example, N-glycosylation sites in eukaryotic proteins are characterized by an amino acid triplet Asn-X-Y, wherein X is any amino acid except Pro and Y is Ser or Thr. Appropriate substitutions, additions or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846.

Antigen-Binding Domain

This describes the part of an antibody molecule which comprises the area which specifically binds to and is complementary to part or all of an antigen. Where an antigen is large, an antibody may only bind to a particular part of the antigen, which part is termed an epitope. An antigen binding domain may be provided by one or more antibody variable domains (e.g. a so-called Fd antibody fragment consisting of a VH domain). Preferably, an antigen binding domain comprises at least a substantial portion of an antibody light chain variable region (VL) and at least a substantial portion of an antibody heavy chain variable region (VH).

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of target binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as discussed in more details below.

Comprise

This is generally used in the sense of include, that is to say permitting the presence of one or more features or components.

Isolated

This refers to the state in which VH domains, target binding members of the invention, or nucleic acid encoding such binding members, will generally be in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo.

Target binding members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Target binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

Additional Features of Target Binding Members.

In addition to antibody sequences, a target binding member according to the present invention may comprise other amino acids, e.g. forming a peptide or polypeptide, such as a folded domain, or to impart to the molecule another functional characteristic in addition to ability to bind antigen. Target binding members of the invention may carry a detectable label, or may be conjugated to a toxin or enzyme (e.g. via a peptidyl bond or linker).

Detectable labels include radiolabels such as 131I or 99Tc, which may be attached to antibodies of the invention using conventional chemistry known in the art of antibody imaging. Labels also include enzyme labels such as horseradish peroxidase. Labels further include chemical moieties such as biotin which may be detected via binding to a specific cognate detectable moiety, e.g. labelled avidin.

Where the additional feature is a polypeptide domain or label, the target binding member may be produced by recombinant techniques, i.e. by the expression of nucleic acid encoding a fusion of the target binding member and the further domain.

Chain Shuffling

A further aspect of the invention provides a method for obtaining an antibody antigen-binding domain for IL-25, the method comprising providing combining a VH domain of a target binding member of the invention with one or more VL domains, and testing the VH/VL combination or combinations for antibody-antigen binding domain for IL-25.

Said VL domain may have an amino acid sequence which is substantially as set out herein.

An analogous method may be employed in which one or more sequence variants of a VL domain disclosed herein are combined with one or more VH domains.

This may be achieved by phage display screening methods using the so-called hierarchical dual combinatorial approach as disclosed in WO92/01047 in which an individual colony containing either an H or L chain clone is used to infect a complete library of clones encoding the other chain (L or H)

and the resulting two-chain target binding member is selected in accordance with phage display techniques such as those described in that reference.

Thus the present invention provides a method for selection of an antibody molecule for IL-25, the method comprising:
(a) providing a VH domain comprising a target binding member that binds IL-25 and which comprises an antibody VH domain of the present invention;
(b) combining said VH domain with a plurality of antibody VL domains to provide antibody molecules;
(c) screening said antibody molecules for binding to IL-25; and
(d) selecting an antibody molecule which binds IL-25.

In such a method, the VH and VL domains may be provided in the form of proteins expressed by recombinant DNA, particularly by a phage or phagemid DNA.

The plurality of VL domains may be anything from 104 individual domains upwards, for example from 106 to 108 or 1010 domains.

Antibody molecules, and nucleic acid encoding such molecules, may form a further part of the present invention.

IL-25

Il-25, also referred to in the art as IL-17E, is available from commercial sources (e.g. R&D Systems, MN, USA) or may be cloned or synthesised by reference to the sequences of IL-25 available in the art. Murine IL-25 (NCBI Protein NP_542767) is described by Hurst et al, 2002 (Ref. 7 below). Human IL-25 (NCBI Protein Q9H293) is described by Fort et al (Ref. 4 below). For production of antibodies or use in immunoassays, fragments of recombinant IL-25 may be used, particularly those truncated at the N-terminal. For example, commercially available recombinant human IL-25 (IL-17E) comprises the mature protein sequence of Tyr 33-Gly 177 of Accession No. Q9H293) and commercially available murine IL-25 comprises residues Val 17-Ala 169 of mouse IL-17E (Accession No. NP_542767).

Nucleic Acids and Vectors

In further aspects, the invention provides an isolated nucleic acid which comprises a sequence encoding a target binding member, a VH domain, or VL domain according to the present invention, and methods of preparing a target binding member, a VH domain, or a VL domain of the invention, which comprise expressing said nucleic acid under conditions to bring about production of said target binding member, VH domain, or VL domain, and recovering it.

The nucleic acids of the invention may comprise the sequences, or relevant portions thereof (e.g. CDR-encoding regions) of SEQ ID NO:40 (for heavy chains) or SEQ ID NO:26 (for light chains), or variants of these sequences modified by, for example, site-directed mutagenesis to encode other VH and VL domains of the invention. Further, codon usage may be varied, e.g. to optimize expression of the sequence in a desired host cell.

The present invention further provides an isolated nucleic acid encoding a target binding member of the present invention. Nucleic acid includes DNA and RNA.

Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

The present invention also provides vectors, for example in the form of plasmids, viruses, e.g. 'phage, or phagemid, cosmids, transcription or expression cassettes which comprise at least one nucleic acid as above.

Suitable vectors can be chosen or constructed, containing appropriate regulatory sequences, including promoter sequences, terminator sequences, polyadenylation sequences, enhancer sequences, marker genes and other sequences as appropriate. For further details see, for example, Molecular Cloning: a Laboratory Manual: 2nd edition, Sambrook et al., 1989, Cold Spring Harbor Laboratory Press.

Vectors of the invention also include viral vectors capable of infecting human cells in vivo, e.g. adenoviral, retroviral or adeno-associated virus vectors. Such vectors may be useful for expression of a target binding member of the invention in the cells of a human or animal subject, to provide for production and delivery of the target binding member to said subject.

A nucleic acid sequence encoding a target binding member of the invention will in one aspect be operably linked to a promoter to effect expression of the target binding member in a host cell. The sequence may include at its 5' end a leader sequence to facilitate expression and/or secretion of the target binding member in and/or from a host cell. Numerous suitable leader sequences are known as such in the art and may be selected by a person of ordinary skill in the art taking account of the host cell.

Suitable leader sequences include any human or other mammalian immunoglobulin leader sequence, although a non-immunoglobulin mammalian leader sequence or a synthetic leader sequence could be used instead. Preferably for expression of a VH chain a human VH leader sequence may is used. Preferably for expression of a VL chain a human VL leader sequence is used.

A suitable leader sequence for expression of a VH domain of the invention is:

MGSTAILGLLLAVLQGVCA.    (SEQ ID NO: 37)

A suitable leader sequence for expression of a VL domain of the invention is a human or murine VK leader sequence. Such a sequence may be the 2C3 leader sequence:
MRVPAQLLGLLLLWLPDTRC (SEQ ID NO:38) or a human homologue, such as MDMRVPAQLLGLLLLWLPDTRC (SEQ ID NO:39).

In the accompanying examples we have used expression constructs that include a HindIII site and consensus Kozak sequence (AAGCTTGCCGCCACC, SEQ ID NO:41) preceding the coding sequence that commences with an antibody leader sequence. This is suitable for expression of the antibody domains in mammalian host cells. However, other constructs may be used depending upon the preference of the experimenter and the host cell in which the antibody domain is to be expressed.

Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992. The disclosures of Sambrook et al. and Ausubel et al. are incorporated herein by reference.

Host Cells and Production of Target Binding Members

A further aspect provides a host cell transformed with a nucleic acid (e.g. a nucleic acid sequence in the form of a vector) of the invention.

In one embodiment, the nucleic acid of the invention is integrated into the genome (e.g. chromosome) of the host cell. Integration may be promoted by inclusion of sequences which promote recombination with the genome, in accordance with standard techniques.

A yet further aspect provides a method of production of a target binding member of the invention, the method including causing expression from encoding nucleic acid. Such a method may comprise culturing host cells under conditions for production of said target binding member.

Following production by expression a VH or VL domain, or target binding member may be isolated and/or purified using any suitable technique, then used as appropriate. A method of production may comprise a step of isolation and/or purification of the product.

Following purification of the product the target binding member may be modified by physical or chemical means, for example to introduce protective groups that alter, e.g. increase, the stability or biological half-life of the protein. For example, PEGylation of proteins to achieve such effects is known as such in the art and target binding members of the invention may be in PEGylated form.

A method of production may comprise formulating the product into a composition including at least one additional component, such as a pharmaceutically acceptable excipient.

The present invention also provides a recombinant host cell which comprises one or nucleic acids or vectors as above. A nucleic acid encoding any CDR, VH or VL domain, or target binding member as provided itself forms an aspect of the present invention, as does a method of production of the encoded product, which method comprises expression from encoding nucleic acid therefor.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NS0 mouse melanoma cells, YB2/0 rat myeloma cells and many others. A common, preferred bacterial host is *E. coli*.

The expression of antibodies and antibody fragments in prokaryotic cells such as *E. coli* is well established in the art. For a review, see for example Plückthun, A. Bio/Technology 9: 545-551 (1991). Expression in eukaryotic cells in culture is also available to those skilled in the art as an option for production of a target binding member, see for recent reviews, for example Ref, M. E. (1993) Curr. Opinion Biotech. 4: 573-576; Trill J. J. et al. (1995) Curr. Opinion Biotech 6: 553-560.

Compositions

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Therapeutic formulations of the target binding member may be prepared for storage by mixing the target binding member having the desired degree of purity with optional physiologically acceptable carriers, excipients, or stabilizers (see e.g. "Remington: The Science and Practice of Pharmacy", 20th Edition, 2000, pub. Lippincott, Williams & Wilkins.), in the form of lyophilized powder or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

For the target binding member to be used for in vivo administration it must be sterile. This is readily accomplished by filtration through sterile filtration membranes, prior to or following lyophilization and reconstitution. The target binding member ordinarily will be stored in lyophilized form or in solution.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Therapeutic Uses of the Invention

The present invention provides for the first time a demonstration that antibodies against IL-25 are effective in preventing or reducing airway hyperresponsiveness in vivo, a key symptom of asthma. Thus in one aspect the invention provides a method of preventing or reducing airway hyperresponsiveness in a subject (e.g. a human) in need of treatment which comprises administering to the subject a target binding member, particularly an antibody molecule, that binds IL-25. In another aspect the invention provides a method of preventing, reducing or treating asthma in a subject in need of treatment which comprises administering to the subject a target binding member, particularly an antibody molecule, that binds IL-25. Asthma includes allergic asthma.

The above methods may be practiced with target binding members (including compositions thereof) according to the present invention, which are useful in binding to and preferably antagonising action of IL 25, with therapeutic potential in various diseases and disorders in which IL-25 plays a role. In addition to asthma, such diseases include other conditions associated with inflammation, such as Crohn's disease and ulcerative colitis. The methods may also be practiced with other target binding members (including compositions thereof) which bind IL-25 that may be obtained as described below in the accompanying examples.

Target binding members (including compositions thereof) according to the invention may be used in a method of treatment (including prophylactic treatment) or diagnosis in human or animal subject. Such a method of treatment or diagnosis (which may include prophylactic treatment) may comprise administering to said subject an effective amount of a target binding member of the invention. Exemplary diseases and disorders are discussed further below.

Also provided is the use of a target binding member (including a compositions thereof) of the invention in the manufacture of a medicament for administration, to a human or animal subject.

Clinical indications in which an anti-IL-25 target binding member may be used to provide therapeutic benefit include any condition in which IL-25 has pathological consequences. Thus in general, the target binding member of the invention may be used in the treatment of any condition associated with an unwanted Th2 response or type-2 responses. For example, the target binding member of the invention may be used for the treatment of allergy and asthma, particularly asthma.

Anti-IL-25 treatment may be given by injection (e.g. intravenously) or by local delivery methods. Anti-IL-25 may be delivered by gene-mediated technologies. Alternative formulation strategies may provide preparations suitable for oral or suppository route. The route of administration may be determined by the physicochemical characteristics of the treatment, by special considerations for the disease, to optimise efficacy or to minimise side-effects.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors. Appropriate doses of antibody are well known in the art; see Ledermann J. A. et al. (1991) Int. J. Cancer 47: 659-664; Bagshawe K. D. et al. (1991) Antibody, Immunoconjugates and Radiopharmaceuticals 4: 915-922.

The precise dose will depend upon a number of factors, including whether the antibody is for diagnosis or for treatment, the size and location of the area to be treated, the precise nature of the antibody (e.g. whole antibody, fragment or diabody), and the nature of any detectable label or other molecule attached to the antibody. A typical antibody dose will be in the range 0.5 mg-1.0 g, and this may be administered intravenously as a bolus or as an infusion over several hours as appropriate to achieve the required dose. Other modes of administration include intravenous infusion over several hours, to achieve a similar total cumulative dose. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

A further mode of administration employs precoating of, or otherwise incorporation into, indwelling devices, for which the optimal amount of antibody will be determined by means of appropriate experiments.

An antibody molecule in some preferred embodiments of the invention is a monomeric fragment, such as F(ab) or scFv. Such antibody fragments may have the advantage of a relatively short half life and less risk of platelet activation, which may be caused by receptor clustering. Clustering which gives rise to platelet activation could be either of IL-25 molecules or of IL-25 with FcγRII molecules, for instance.

If a whole antibody, is used, it is preferably in a form that is unable to activate and/or destroy platelets. The IgG4 isotype or alternatively "designer" isotypes derived from the IgG1 backbone (novel Fc gene constructs WO99/58572, Clark, Armour, Williamson) are preferred choices. Smaller antibody fragments may be used, such as F(ab')2. In addition, whole antibodies or fragments (e.g. F(ab')2 or diabodies) with dual epitope specificity (e.g. for the epitopes recognised by scFv 2C3) may be used. Although such an embodiment may promote receptor clustering, a high association rate to individual receptors may rule out this problem.

Target binding members of the present invention will usually be administered in the form of a pharmaceutical composition, which may comprise at least one component in addition to the target binding member.

A target binding member of the invention may be administered alone or in combination with other treatments, either simultaneously or sequentially dependent upon the condition to be treated. Other treatments may include the administration of suitable doses of pain relief drugs such as non-steroidal anti-inflammatory drugs (e.g. aspirin, paracetamol, ibuprofen or ketoprofen) or opiates such as morphine; the administration of anti-emetics; or the administration of at least one other compound active against asthma, generally a bronchodilating agent which produces airway relaxation or enhances mucus clearance, e.g. a beta-agonist (e.g. salbutamol, salmeterol), disodium cromoglycate, steroids or an inhibitor of PDEIV.

Assay Methods

The present invention provides a method comprising causing or allowing binding of a target binding member as provided herein to IL-25. As noted, such binding may take place in vivo, e.g. following administration of a target binding member, or nucleic acid encoding a target binding member, or it may take place in vitro, for example in ELISA, Western blotting, immuno-cytochemistry, immuno-precipitation or affinity chromatography.

The amount of binding of target binding member to IL-25 may be determined. Quantitation may be related to the amount of the antigen in a test sample, which may be of diagnostic interest.

The reactivities of antibodies on a sample may be determined by any appropriate means. Radioimmunoassay (RIA) is one possibility. Radioactive labelled antigen is mixed with unlabelled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual antibody-reporter conjugates may be used to derive quantifiable absolute or relative data of the relevant antibody binding in samples (normal and test).

The present invention also provides the use of a target binding member as above for measuring antigen levels in a competition assay, that is to say a method of measuring the level of antigen in a sample by employing a target binding member as provided by the present invention in a competition assay. This may be where the physical separation of bound from unbound antigen is not required. Linking a reporter molecule to the target binding member so that a physical or optical change occurs on binding is one possibility. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

The present invention also provides for measuring levels of antigen directly, by employing a target binding member according to the invention for example in a biosensor system.

The mode of determining binding is not a feature of the present invention and those skilled in the art are able to choose a suitable mode according to their preference and general knowledge.

EXAMPLES

Aspects and embodiments of the present invention will now be illustrated by way of example with reference to the following experimentation.

Comparative Example

The Primary Sequence of 2c3

The kappa light chain sequence excluding its leader sequence is shown in FIG. 1 (SEQ ID NO:15) and the amino acid sequence of the CDRs loops, as defined by Kabat, named L1 (SEQ ID NO:29), L2 (SEQ ID NO:30) and L3 (SEQ ID NO:31). It is the L1, 2 and 3 sequences that were the donor sequence for the humanisation of the 2c3 light chain. The sequence of the heavy chain (SEQ ID NO:17) is shown in FIG. 2 and again the CDRs are identified as H1 (SEQ ID NO:32), H2 (SEQ ID NO:35) and H3 (SEQ ID NO:33).

Analysis of 2c3 Heavy and Light Chains

A database of human antibody sequences was analysed to identify acceptor framework sequences for 2c3. The database of human antibody sequences comprises of 9597 heavy chain sequences and 2695 light chain sequences. Suitable acceptor sequences were preliminarily identified on the basis of firstly the highest VCI score, secondly framework (FR) score and thirdly identity score. Finally, any sequences that failed to have conserved loop lengths for H1 H2, L1 and L2 were discarded. The top 20 human antibody sequences were subsequently checked to eliminate humanised antibodies, heavily mutated scFv antibodies and mouse antibodies. Those sequences with Cysteine or Proline residues in atypical positions were also eliminated.

Analysis of the Heavy Chain Acceptor for 2c3

The top 20 sequences for the 2c3 heavy chain were identified. The sequence, AY393094, with the top VCI score (SEQ ID NO:19), with only 2 different VCI residues A67V and L69I is shown in FIG. 3. Both these are conservative changes. The analysis of the rest of the framework sequence shows 59 out of 87 residues are conserved. The interface residues found in 2c3 and AY393094 are conserved in the cognate heavy chain (AY510106) for our proposed light chain AY510106. Altogether the analysis makes AY393094 (SEQ ID NO:19) a good candidate that may require few VCI back mutations.

However AY393094's H3 loop length is 17 rather than the 13 residues found in 2c3 but this difference in the length of H3 is not uncommon during humanisations and is deemed less important than conserving the VCI residues.

The Humanised Construct of the Heavy Chain of 2c3 (RHA)

The humanised heavy chain construct is shown in FIG. 4 and was named RHA (SEQ ID NO:21). The leader sequence and framework sequence are from AY393094 and H1-3 loops as defined by Kabat are from 2c3. At the 5' end a consensus Kozak sequence and a HindIII restriction site has been added while at the 3' end an ApaI restriction site has been added. The restriction sites are to assist the expression vectors and the Kozak consensus sequence is intended to maximise protein expression. N-linked glycosylation sites have the motif NX(S/T), none were found in the humanised heavy chain. The quality of the peptide cleavage site was assessed by applying the Signal P program to the amino terminal peptide sequence of RHA. The results confirmed that the VH5a leader sequence will cleave between VCA (the C-terminal end of the signal peptide) and EVR (the N-terminal end of FR1).

Light Chain Framework Analysis

A number of human light chain frameworks with the best VCI and framework scores were identified. However, after consideration of the three top-scoring sequences, all were discounted. The first because this light chain was from an antibody that has been shown to associate with amyloid fibril formation, the next two as the sequences have non conserved residues at positions 1 and 3. The inventors' previous experience of humanisation led them to believe that these residues should be conserved.

The next best sequences only differed in two VCI residues V44P and Y71F, though on further analysis noted that candidates with the highest framework scores were very similar but have either L73F or I83F mismatches. Phenylalanine is a relatively large change and appears to be conserved in these two types of light chains. Further analysis of 2c3-like light chain frameworks found a significant number that have a valine at position 83 combined with leucine at position 73 and thus provides an alternative to those frameworks with a Phe at position 83. In view of this the inventors selected a light chain, AY510106, which is a V83 light chain with the same CDR loop lengths as 2c3. The sequence for AY510106 (SEQ ID NO:23) is shown in FIG. 5.

The Humanised Construct of the Light Chain of 2c3 (RKA)

The humanised kappa light chain construct is shown in FIG. 6 and named RKA (SEQ ID NO:25). The leader sequence and framework sequence are from AY510106 and L1-3 is from 2c3. At the 5'-end a consensus Kozak sequence and a HindIII restriction site has been added while at the 3'-end a BamHI restriction site and splice site has been added. The restriction sites and splice sites are necessary to clone and express the construct in pKN100 expression vector and the Kozak consensus sequence is intended to maximise protein expression. N-linked glycosylation sites have the motif NX(S/T), none were found in the humanised light chain. The quality of the peptide cleavage site was assessed by applying the Signal P program to the amino terminal peptide sequence of 2c3 RKA. The results confirmed that the VK1-A20 leader sequence was cleaved between the residues TRC (at the C-terminal end of the signal peptide) and DI (at the N-terminal end of FR1).

Comparison of RHA and RKA to Chimeric 2c3

The humanised 2c3 heavy chain RHA and kappa light RKA cDNAs were synthesised (GeneArt AG) and cloned into the IgG1 heavy chain expression vector pG1D200 and the light chain expression vector pKN100, respectively. Initially, heavy and light chain cDNA constructs from chimeric 2c3 and the humanised antibody were combined and used to transiently transfect HEK293T cells. The supernatants from the transfected cells were used in an ELISA to measure antibody binding to IL-25. The results (FIG. 7(A)) indicated that humanised antibody comprising chimeric 2c3 light chain with humanised heavy chain, RHA, bound significantly less to IL-25 than antibody comprising chimeric 2c3 light and heavy chains. In contrast, equivalent binding to IL-25 was found for the humanised light chain, RKA, or chimeric 2c3 light chain associated with chimeric 2c3 heavy chain.

In an attempt to recover maximum binding for the humanised heavy chain, the VCI residues A67V and I69L were replaced by mutagenesis. The antigen binding of the double mutant RHA_A67V_I69L and RHA_I69L combined with the light chain RKA was compared to that of chimeric 2c3. HEK 293T cells were co-transfected with the various mutagenised heavy chains and RKA and the supernatant used in an IL-25 binding ELISA. The results shown in FIG. 7(B) show that maximal antibody binding to IL-25 was only partially recovered by the replacement of both A67V and I69L residues.

Further mutagenesis was carried out on RHA. The amino acid replacements R3Q, S82aL were made and the supernatants from transiently transfected HEK293T cells were used in an IL-25 binding ELISA. The results in FIG. 7(C) show that these replacements had little or no effect on improving the humanised antibody binding to IL-25.

The conclusion therefore was that the light chain humanisation was successful and did not require further modification whereas even with further engineering of the heavy chain the humanisation based upon transfer of the CDRs into a heavy chain with apparently well conserved VCI residues was unsuccessful.

Example 1

Design of High Affinity Humanised Antibody

The framework AY393094 failed to provide a satisfactory humanised antibody despite the replacement of vernier or canonical residues, giving antibody framework regions with a high sequence identity priority over VCI score. This method identified a different class of human frameworks. Of these, the one with the highest VCI score was selected. Its leader sequence was unknown so that of the VH5a leader sequence was used as a replacement. The sequence of the human VH domain selected, AJ399823 (SEQ ID NO:27), is shown in FIG. 8.

Its CDRs were replaced with those of 2c3 and the second humanised antibody was termed RH2. The sequence is shown as SEQ ID NO:4. RH2 has five non conserved VCI residues: Ser 30; Met 48; Val 67; Arg 71 and Thr 73 (Kabat numbering). These residues are referred to below as b, c, d, e and f respectively.

The humanised heavy chain containing all the VCI replacements was termed RH2bcdef and was tested in association with the light chain RKA. The supernatants from transiently transfected HEK293T cells were used in an IL-25 binding ELISA. A comparison between RHA and RH2bcdef showed improved binding to IL-25 compared to RHA, but failed to recapture 100% binding exhibited by the chimeric 2c3. The conclusion therefore was that an alternative approach to the straightforward humanisation of 2c3 was required.

Example 2

CDR Modification of RH2bcdef

Two CDR residues were found to improve potency of the humanised antibody. The mutations D31G and G96D were introduced into RH2bcdef and used to transiently transfected HEK293T cells. The supernatants were used in an IL-25 binding ELISA. The results in FIG. 9(A) show that the D31G mutation recovers the potency RH2bcdef to the levels of 2c3. However the G96D mutation, FIG. 9(B), increases antigen binding potency substantially beyond that of 2c3.

To test if the two mutations were additive both were incorporated into RH2bcdef. Supernatants from transiently transfected HEK293T cells were used in an IL-25 binding ELISA. The results shown in FIG. 10 suggest that there is a small but significant increase in potency humanisation by incorporating both CDR mutations.

Our data also indicate that in addition to Gly or Asp, position 31 could also be selected from Ala, Ser, Val, Asn, Lys, Tyr or Met to maintain similar binding properties of the antibody.

Example 3

Residue 96 (Kabat) Modifications

In order to better understand which amino acids can be tolerated at residue 96 the glycine was replaced by mutagenesis by representative selection of amino acids. The following mutations were made to RH2bcdef: G96Y, G96N, G96S, G96L, G96K and G96E. The expression constructs were co-transfected with RKA into HEK293T cells and the supernatants were used in an IL-25 binding ELISA. The results showed that only the substitution of aspartate at position 96 by asparagine was of equivalent potency, all the other residues tested at this position had a detrimental effect on binding to IL-25. Surprisingly a detrimental effect on potency also included the substitution by glutamate which is a negatively charged residue, similar to aspartate. It may be concluded that the negative charge is not the prime contribution aspartate makes to the increase in potency.

Accordingly, residue 96 (Kabat) in a VH domain of the invention may be aspartate or asparagine.

Example 4

Determining the Minimal Requirement of Mouse VCI Residues for RH2

In order to minimise the potential immunogenic impact on the humanised antibody it is desirable to minimise the number of murine amino acid framework replacements. The humanised heavy chain RH2bcdef G96D was named RH2.1 and had five VCI replacements from 2c3. Initially four were removed to identify which residues contributed to potency.

Mutations c, d, e, and f were replaced with the endogenous human framework residue as single mutations. HEK 293T cells were co-transfected with the VCI mutations and RKA and the supernatants were tested in an IL-25 binding ELISA. Surprisingly it was found that re-introducing the human residues V67 or T73 had a slight enhancement of potency which was unexpected. Changing Met at 48 back to the murine Ile did not have any significant effect.

However, the presence the human arginine residue at position 71 appeared to have a detrimental effect on binding to IL-25. Therefore the conclusion was that only the murine VCI residue Val 71 was very desirable in the humanised antibody. The other residues may be either mouse or human.

In order to identify an optimal final humanised heavy chain a new version of the heavy chain was synthesised called RH2.5 (SEQ ID NO:4) that contained no murine VCI residues. In addition, two modified versions of RH2.5 were made with either the VCI mutations S3OT (SEQ ID NO:3) or R71V (SEQ ID NO:2). The binding of these three new humanised antibodies to IL-25 were analysed by ELISA. The results are shown in FIG. 11. It was found that in comparison to RH2.5 the addition of S30T or R71V enhanced binding to human IL-25 equally.

Therefore in some embodiments of the invention the positions 30 and 71 of the heavy chain may be modified, separately or in combination, from S to T and R to V respectively.

Example 5

Antibody Thermostability

The thermostability of RH2.5_S30T (SEQ ID NO:3) and RI-12.5_R71V (SEQ ID NO:2) was determined. Antibodies were held at various temperatures for 10 minutes then rapidly cooled to room temperature and their ability to bind IL-25 was measured by ELISA. It was found that the 2c3 chimeric antibody (control) retains greater thermostability and is active up to temperatures of 75° C. RH2.5_R71V remained active up to 65° C. and RH2.5_S30T was active up to 60° C.

Example 6

Non B/non T Cells Bio-assay of the Humanized Antibodies

There are few in vitro bio-assays available to measure IL-25 activity. One potent assay is measuring IL-13 release from Non B/non T (NB/NT) cells isolated from the mesenteric lymph nodes of mice. In this assay cells were incubated with IL-25 and varying concentrations of antibody, and IL-13 was measured three days post stimulation. The results showed that the murine 2c3 antibody only partially inhibited IL-13 production. In contrast, RH2.5_R71V and S30T both ablate IL-13 production and RH2.5 significantly reduced IL-13 production. Interestingly RH2.5_R71V and RH2.5_S3OT both still showed complete inhibition of IL-13 production at concentrations as low as 0.25 µg/ml but some small levels of cytokine production can be found for RH2.5 at this concentration. These data are consistent with the notion that the humanised antibody is more potent than the 2c3 chimeric antibody and that the mutations R71V and S30T have enhanced antigen binding potency.

Example 7

RH2.5-R71V Inhibits Airways Hyper-Responsiveness

In further experiments, the humanised antibody RH2.5_R71V was tested in a mouse model of acute airways hyper-responsiveness (AHR). The experimental protocol is summarised in FIG. 12. Mice were initially sensitised to ovalbumin then challenged in the presence of the anti-IL-25 antibodies. The results in FIG. 13(A) show that the AHR response was blocked by the addition of 500 µg dose per mouse of 2c3 but not blocked when the dose was lowered to 50 µg dose per mouse. In contrast, AHR was blocked using only a 50 µg dose (2.5 mg/Kg) of the humanised antibody RH2.5_R71V as shown in FIG. 13(B). These data further support the view that the humanised antibody is significantly more potent than the 2c3 antibody.

Example 8

Colitis Treatment

To presensitize female BALB/c mice (10 per group) a field of the abdominal skin was shaved, and 150 µl of a 3% (w/v) solution of oxazolone in 100% ethanol was applied. Control mice were presensitized by application of 150 µl of 100% ethanol. 7 days after presensitization, mice were rechallenged intrarectally with 150 µl of 3% oxazolone in 50% ethanol or 50% ethanol only (control), under anaesthesia with isoflurane. To ensure distribution of the oxazolone within the entire colon and cecum, mice were held in a vertical position for 1 minute after the injection. An antibody that is a chimaera of the mouse 2C3 sequence in a human IgG1 backbone (100 µg/dose) was administered intraperitoneally (i.p.) on both the day before presensitization and the day before intrarectal (i.r.) administration of oxazolone. Control mice received isotype control human IgG4 (100 µg/dose). All animal experiments outlined here were undertaken with the approval of the UK Home Office.

Colon length was measured in groups of mice following three daily administrations of either 50% ethanol plus IgG4 isotype control i.p. (50% EtOH IgG4); 50% ethanol i.r. plus anti-IL-25 i.p. (50% EtOH Anti-IL-25); 50% ethanol with 3% oxazolone i.r. plus IgG1 isotype control i.p. (3% oxazolone IgG4) and 50% ethanol with 3% oxazolone i.r. plus anti-IL-25 i.p. (3% oxazolone Anti-IL-25).

Animal weights were measured daily following treatment as above.

FIG. 14A shows that administration of oxazolone induces a reduction in colon length as an indicator of colitis. The animals treated with oxazolone and 2C3-derived anti-IL-25 antibody show a trend towards longer colons (an improved prognosis) relative to the oxazolone and IgG4-isotype-treated animals. Treatment with oxazolone also induces weight loss in comparison to the vehicle only control (FIG. 14B). The animals treated with oxazolone and anti-IL-25 also lose weight though show a trend to regain weight more rapidly than the oxazolone IgG4-isotype-treated group at day 3.

Materials and Methods

Abbreviations
AHR Airways hyperreactivity
° C. Centigrade
bp Base pairs
DMEM Dulbecco's Modified Eagles Medium
DMSO Dimethyl sulphoxide
DNA Deoxyribonucleic acid
ELISA Enzyme linked immuno-adsorbent assay
FCS Foetal calf serum
FR Framework
g Grams
HEK 293T Human embryonic kidney cells expressing SV40 large
T antigen (HEK 293T cells)
hr Hour
HRP Horseradish peroxidase
IgG Immunoglobulin mAb Monoclonal antibody
min Minute
NB/NT Non B/Non T cells isolated from mouse mesenteric lymph nodes
NIMR National Institute for Medical Research (UK)
nm Nanometer
OD Optical density
PBS Phosphate buffered saline
PCR Polymerase chain reaction
RH Recombinant heavy chain
RK Recombinant kappa chain
RT Room temperature
sec Second
UV Ultra violet
VH Immunoglobulin heavy chain variable region
VL Immunoglobulin light chain variable region
VK Immunoglobulin kappa light chain variable region
Immunology and Molecular Biology Reagents

| Article | UK Supplier | Catalog Number | Lot Numbers |
|---|---|---|---|
| 10β competent E. coli cells | NEB | C3019H | |
| Agarose (UltraPure ™) | Invitrogen | 15510-027 | 3048948 |
| Albumin bovine (BSA) | Sigma | A7030 | 086K1230 |
| Ampicillin | Sigma | A-9518 | 63H0992 |
| Antarctic Phosphatase | NEB | M0289S | 13 |
| Apa I | Promega | R636 | 20381008 |
| Bam HI | Promega | R602 | 21936309 |
| Carbonate-Bicarbonate buffer | Sigma | C3041 | 076k82206 |
| FuGENE ® 6 Transfection Reagent | Roche | 11814443001 | 14069500 |
| Go-Taq green polymerase | Promega | | |
| Goat anti-human IgG (Fc fragment specific) antibody | Stratech Scientific | 109-005-098 | 76111 |
| Goat anti-human kappa chain horseradish peroxidase conjugate | Sigma | A7164 | 116K6101 |
| Hind III | Promega | R604 | 19453528 |
| Human IgG1/kappa antibody. | The Binding Site | BP078 | 247317 |
| IL-25 (murine) | R&D Systems | | |
| IL-25 (human) | R&D Systems | | |
| K-Blue HRP substrate | SkyBio | 308176 | 080129 |
| MiniElute Gel Extraction kit | Qiagen | 28606 | 124105586 |
| Oligonucleotides | Sigma | n.a. | |
| PBS Tablets | Sigma | P4417 | 017K8212 |
| Phusion ™ Site-Directed Mutagenesis Kit | NEB (Finnzymes) | F-541S | |
| QIAGEN Plasmid Maxi Kit (25) | Qiagen | 12163 | 127142067 |
| QIAprep Spin Miniprep Kit | Qiagen | 27106 | 127150290 |
| Quantikine Murine IL-13 ELISA Kit | R&D Systems | M1300CB | |
| Quick Ligation Kit | NEB | M2200s | |
| QuikChange ® II XL Site-Directed Mutagenesis Kit | Stratagene | 200522-5 | 0870486 |
| Red Stop Solution (For K Blue) | SkyBio Ltd | 301475 | 071114 |
| streptavidin-labelled dynabeads | Invitrogen | | |
| SYBR Safe DNA gel stain | Invitrogen | 33102 | 55081A |
| TOPO-TA Cloning ® kit | Invitrogen | 45-0641 | 1311906 |
| X-Gal | Promega | V394A | 20965701 |

Cloning of Chimeric and Humanised Antibody Variable Genes

The heavy and light chain variable region cDNAs of the 2c3 and the variable region cDNAs of the humanised antibodies were synthesised (GeneArt AG). The heavy chain V regions were cloned into pG1D200 via HindIII and ApaI restriction enzyme sites. Similarly, the light chain V regions were cloned into pKN100 via the HindIII and BamHI sites. pG1D200 vector was prepared for ligation by digesting 5 μg of DNA with 20 units of HindIII and ApaI in multicore (Promega) restriction digest buffer for 2 hrs at 37° C. Subsequently, 1 unit of Antarctic alkaline phosphatase (NEB) was added to the DNA and incubated for between 15 to 30 minutes following manufacturer's instructions. The vector preparation was then purified on a Qiaquick (Qiagen) column following manufacturer's instructions. The vector was eluted in 50 μl. Similarly pKN100 vector was prepared by digesting 5 μg of DNA with 20 units of HindIII and BamHI in buffer E (Promega) for 1 hour at 37° C. The DNA was treated with Antarctic alkaline phosphatase and purified as described above. V region insert DNAs (approx 4 μg) were digested as described above and the heavy and light chain fragments were purified from the vector by gel electrophoresis. The appropriate band was excised from the gel and purified on a Qiaquick column (Qiagen) and eluted in 50 μl following manufacturer's instructions. Ligations were carried out by mixing 1 μl of vector with either 1 μl or 3 μl of insert DNA in 1×Quick ligase buffer (NEB) and 1 μl of NEB Quick Ligase and incubated for 10 minutes at room temperature (20° C.). The reaction was used to transform 50 μl of 10β competent cells (NEB). The vector constructs were confirmed by DNA sequencing and carried out by GATC Biotech Ltd (Cambridge).

Synthesis of Variable Genes and Site-Directed Mutagenesis

Variable Genes were Synthesised by GeneArt AG (Regensburg, Germany)

Site directed mutagenesis was carried out by using QuickChange® II XL Site-Directed Mutagenesis Kit (Stratagene) following the manufacturers instructions. Except for the RHA mutations R3Q and L82aS where the Phusion™ Site-Directed Mutagenesis Kit (NEB) method was used following manufacturers instructions.

IgG1 ELISA

Maxisorp plates were coated with 0.4 μg/ml goat anti-human IgG antibody and stored at 4° C. for no more than 1 month. Before use, plates were washed three times in PBS/0.02% Tween 20 (v/v) then blocked in PBS/0.02% Tween 20 (v/v)/0.2% (w/v) BSA. Plates were washed as before and sample supernatant added over a concentration range using doubling dilutions and incubated at 37° C. for 1 hr. Plates were washed as before and incubated with goat anti-human kappa light chain peroxidase conjugate (Sigma) at 1:5000 dilution. Plates were washed, as before, then 150 μl of K Blue One-Step substrate (Neogen) was added. After 10 minutes the reaction was stopped with 50 μl of Red Stop solution (Neogen) and the optical density was measured at 655 nm.

Cytokine Binding Assays

Maxisorp plates were coated with 0.25 μg/ml human IL-25 (R&D systems) in Carbonate-bicarbonate buffer (Sigma) and stored at 4° C. for no more than 1 month. Before use, plates were washed three times in PBS/0.02% Tween 20 (v/v) then blocked in PBS/0.02% Tween 20 (v/v)/0.5% (w/v) BSA. Plates were washed as before and sample supernatant added over a concentration range using doubling dilutions and incubated at 37° C. for 1 hr. Plates were washed as before and incubated with goat anti-human kappa light chain peroxidase conjugate (Sigma) at 1:5000 dilution. Plates were washed, as before, then 150 μl of K Blue One-Step substrate (Neogen) was added. After 10 minutes the reaction was stopped with 50 μl of Red Stop solution (Neogen) and the optical density was measured at 650 nm.

Mice

BALB/c mice were obtained from Harlan UK (Bicester, UK) and maintained in the Small Animal Barrier Unit and Central Biomedical Services LMB Cambridge, facilities in specific pathogen-free environments. All animal experiments outlined in this report were undertaken with the approval of the UK Home Office.

Non B Non T Cells Assays

Non B/non T (NBNT) cells were purified from the mesenteric lymph node and incubated for 72 hours with or without 10 ng/ml rmIL-25, and with either mouse IgG1 isotype (anti-c-myc) or anti-mIL-25 2c3 at varying concentrations of either human IgG1 isotype control (anti-malaria), anti-hIL-25 RH2.5 R71V, anti-hIL-25 RH2.5 S30T, or anti-hIL-25 RH2.5. IL-13 production was assessed from cell supernatant, which was pooled from two duplicate wells, by ELISA. IL-13 ELISA was performed by using the Quantikine Murine IL-13 Kit (R&D Systems).

Experimental Design of the Acute Model of Airways Hyper-Responsiveness (AHR)

BALB/c mice (6-12 weeks) were sensitized by intraperitoneal administration of ovalbumin in PBS (20 µg/injection) complexed with alum, or PBS and alum only (controls), at days 0 and 12. Aerosol administration of 1% ovalbumin was undertaken on days 19, 20, and 21 for 20 minutes per day. Control animals received PBS. Two hours prior to each lung challenge mice also received an intraperitoneal administration of either 2c3, mouse IgG1 control, or human IgG1 isotype control (anti-malaria), or anti-hIL-25 RH2.5 R71V. On day 22, the animals were analyzed by using restrained plethysmography to assess AHR Ovalbumin and antibodies were tested for endotoxin and found to be below 0.1 EU/ml except for RH2.5_R71V that was 1.2 EU/ml.

Measurement of AHR

Animals were anesthetized, tracheostomized, and placed on a ventilator (Minivent 845 ventilator, EMMS, UK) at a rate of approximately 150 breaths/min, with a tidal volume of 0.15 ml. Mice were monitored in a restrained whole-body plethysmograph (EMMS Hants, UK), and transpulmonary pressure was assessed via an inline transducer. After recording stable baseline pulmonary resistance, increasing concentrations of acetyl-β-methylcholine chloride (methacholine; Sigma, Dorset, United Kingdom) were administered by aerosol for 10 seconds with an ultrasonic nebulizer, and pulmonary resistance was recorded for a 3-minute period. EDaq software (EMMS Hants, UK) was used to analyze airways resistance, compliance, and standard pulmonary parameters.

REFERENCES

1. P. G. Fallon et al., Immunity 17, 7 (July, 2002).
2. G. Grunig et al., Science 282, 2261 (1998).
3. M. Wills-Karp et al., Science 282, 2258 (1998).
4. M. M. Fort et al., Immunity 15, 985 (December, 2001).
5. M. R. Kim et al., Blood 100, 2330 (Oct. 1, 2002).
6. G. Pan et al., J Immunol 167, 6559 (Dec. 1, 2001).
7. S. D. Hurst et al., J Immunol 169, 443 (Jul. 1, 2002).
8. T. A. Moseley, et al., Cytokine Growth Factor Rev 14, 155 (April, 2003).
9. P. G. Fallon et al., J Exp Med 203, 1105 (Apr. 17, 2006).
10. A. M. Owyang et al., J Exp Med 203, 843 (Apr. 17, 2006).
11. Jones, P. T., et al., Nature 331:522 (1986).
12. Riechmann, L., et al., Nature 332:323(1988).
13. Chothia, C. & Lesk, A. M. J. Mol. Biol. 196:901 (1987).
14. Foote J & Winter G. J Mol Biol 224:487 (1992).
15. Ballantyne, S. J., et al J. Allergy Clin. Immunol. 120:1324 (2007).
16. Heller, F., et al., Immunity 17, 629-638 (2002)
17. Fichtner-Feigl, S., et al., Mucosal Immunol 1 Suppl 1, S24-7 (2008)
18. Fort, M. M., et al., Immunity 15, 985-995 (2001)
19. Buning, C., et al., Eur J Immunogenet 30, 329-333 (2003)
20. Hanauer, S. B. Aliment Pharmacol Ther 27 Suppl 1, 15-21 (2008)
21. Papa, A., et al., Am J Gastroenterol 104, 1575-1586 (2009)
22. Yun, L., and Hanauer, S. Expert Rev Gastroenterol Hepatol 3, 235-248 (2009)

```
Sequences:
SEQ ID NO: 1-Humanised VH domain (artificial)
Glu Val Gln Leu Val Glu Ser Gly Ala Glu Val Lys Lys Pro Gly Ala Ser Val Lys Val Ser Cys Lys Ala Ser Gly Tyr Ser Phe Xa1 Xa2 Tyr Thr Met Asn Trp Val Arg Gln Ala Pro Gly Gln Arg Leu Glu Trp Xa3

Gly Leu Ile Asn Pro Tyr Asn Gly Gly Thr Ser Tyr

Asn Gln Asn Phe Lys Gly Arg Val Thr Leu Thr Xa4

Asp Thr Ser Ala Ser Thr Ala Tyr Leu Glu Leu Asn

Ser Leu Arg Ser Glu Asp Thr Gly Val Tyr Tyr Cys

Ala Arg Glu Xa5 Tyr Asp Gly Tyr Leu Tyr Phe Ala

Met Asp Tyr Trp Gly Gln Gly Thr Leu Val Thr Val

Ser Ser
``` wherein:
Xa1 is Ser or Thr;
Xa2 is Gly, Asp, Ala, Ser, Val, Asn, Lys, Tyr or Met;
Xa3 is Met or Ile;
Xa4 is Val or Arg; and
Xa5 is Asp, Asn or Gly.

```
SEQ ID NO: 2 - humanised VH domain RH2.5_R71V (artificial)
Glu Val Gln Leu Val Glu Ser Gly Ala Glu Val Lys Lys Pro Gly Ala Ser Val Lys Val Ser Cys Lys Ala Ser Gly Tyr Ser Phe Ser Gly Tyr Thr Met Asn Trp Val Arg Gln Ala Pro Gly Gln Arg Leu Glu Trp Met Gly Leu Ile Asn Pro Tyr Asn Gly Gly Thr Ser Tyr Asn Gln Asn Phe Lys Gly Arg Val Thr Leu Thr Val Asp Thr Ser Ala Ser Thr Ala Tyr Leu Glu Leu Asn Ser Leu Arg Ser Glu Asp Thr Gly Val Tyr Tyr Cys Ala Arg
```

```
Glu Asp Tyr Asp Gly Tyr Leu Tyr Phe Ala Met Asp Tyr Trp

Gly Gln Gly Thr Leu Val Thr Val Ser Ser

SEQ ID NO: 3 - Humanised VH domain RH2.5_S30T (artificial)
Glu Val Gln Leu Val Glu Ser Gly Ala Glu Val Lys Lys Pro Gly Ala Ser Val Lys Val Ser Cys Lys Ala Ser Gly Tyr Ser Phe Thr Gly Tyr Thr Met Asn Trp Val Arg Gln Ala Pro Gly Gln Arg Leu Glu Trp Met Gly Leu Ile Asn Pro Tyr Asn Gly Gly Thr Ser Tyr Asn Gln Asn Phe Lys Gly Arg Val Thr Leu Thr Arg Asp Thr Ser Ala Ser Thr Ala Tyr Leu Glu Leu Asn Ser Leu Arg Glu Asp Thr Gly Val Tyr Tyr Cys Ala Arg Glu Asp Tyr Asp Gly Tyr Leu Tyr Phe Ala Met Asp Tyr Trp Gly Gln Gly Thr Leu Val Val Ser Ser SEQ ID NO: 4 - Humanised VH domain RH2 (artificial)
Glu Val Gln Leu Val Glu Ser Gly Ala Glu Val Lys Lys Pro Gly Ala Ser Val Lys Val Ser Cys Lys Ala Ser Gly Tyr Ser Phe Ser Gly Tyr Thr Met Asn Trp Val Arg Gln Ala Pro Gly Gln Arg Leu Glu Trp Met Gly Leu Ile Asn Pro Tyr Asn Gly Gly Thr Ser Tyr Asn Gln Asn Phe Lys Gly Arg Val Thr Leu Thr Arg Asp Thr Ser Ala Ser Thr Ala Tyr Leu Glu Leu Asn Ser Leu Arg Ser Glu Asp Thr Gly Val Tyr Tyr Cys Ala Arg Glu Asp Tyr Asp Gly Tyr Leu Tyr Phe Ala Met Asp Tyr Trp Gly Gln Gly Thr Leu Val Thr Val Ser Ser SEQ ID NO: 5 - Humanised VH domain (artificial)
Glu Val Gln Leu Val Glu Ser Gly Ala Glu Val Lys Lys Pro Gly Ala Ser Val Lys Val Ser Cys Lys Ala Ser Gly Tyr Ser Phe Thr Gly Tyr Thr Met Asn Trp Val Arg Gln Ala Pro Gly Gln Arg Leu Glu Trp Met Gly Leu Ile Asn Pro Tyr Asn Gly Gly Thr Ser Tyr Asn Gln Asn Phe Lys Gly Arg Val Thr Leu Thr Val Asp Thr Ser Ala Ser Thr Ala Tyr Leu Glu Leu Asn Ser Leu Arg Ser Glu Asp Thr Gly Val Tyr Tyr Cys Ala Arg Glu Asp Tyr Asp Gly Tyr Leu Tyr Phe Ala Met Asp Tyr Trp Gly Gln Gly Thr Leu Val Thr Val Ser Ser SEQ ID NO: 6 - Humanised VH domain (artificial)
Glu Val Gln Leu Val Glu Ser Gly Ala Glu Val Lys Lys Pro Gly Ala Ser Val Lys Val Ser Cys Lys Ala Ser Gly Tyr Ser Phe Ser Asp Tyr Thr Met Asn Trp Val Arg Gln Ala Pro Gly Gln Arg Leu Glu Trp Met Gly Leu Ile Asn Pro Tyr Asn Gly Gly Thr Ser Tyr Asn Gln Asn Phe Lys Gly Arg Val Thr Leu Thr Val Asp Thr Ser Ala Ser Thr Ala Tyr Leu Glu Leu Asn Ser Leu Arg Ser Glu Asp Thr Gly Val Tyr Tyr Cys Ala Arg Glu Asp Tyr Asp Gly Tyr Leu Tyr Phe Ala Met Asp Tyr Trp Gly Gln Gly Thr Leu Val Thr Val Ser Ser
```

-continued

SEQ ID NO: 7 - Humanised VH domain (artificial)
Glu Val Gln Leu Val Glu Ser Gly Ala Glu Val Lys Lys Pro Gly Ala Ser Val Lys Val Ser Cys Lys Ala Ser Gly Tyr Ser Phe Thr Asp Tyr Thr Met Asn Trp Val Arg Gln Ala Pro Gly Gln Arg Leu Glu Trp Met Gly Leu Ile Asn Pro Tyr Asn Gly Gly Thr Ser Tyr Asn Gln Asn Phe Lys Gly Arg Val Thr Leu Thr Arg Asp Thr Ser Ala Ser Thr Ala Tyr Leu Glu Leu Asn Ser Leu Arg Ser Glu Asp Thr Gly Val Tyr Tyr Cys Ala Arg Glu Asp Tyr Asp Gly Tyr Leu Tyr Phe Ala Met Asp Tyr Trp Gly Gln Gly Thr Leu Val Thr Val Ser Ser SEQ ID NO: 8 - Humanised VH domain (artificial)
Glu Val Gln Leu Val Glu Ser Gly Ala Glu Val Lys Lys Pro Gly Ala Ser Val Lys Val Ser Cys Lys Ala Ser Gly Tyr Ser Phe Thr Asp Tyr Thr Met Asn Trp Val Arg Gln Ala Pro Gly Gln Arg Leu Glu Trp Met Gly Leu Ile Asn Pro Tyr Asn Gly Gly Thr Ser Tyr Asn Gln Asn Phe Lys Gly Arg Val Thr Leu Thr Val Asp Thr Ser Ala Ser Thr Ala Tyr Leu Glu Leu Asn Ser Leu Arg Ser Glu Asp Thr Gly Val Tyr Tyr Cys Ala Arg Glu Asp Tyr Asp Gly Tyr Leu Tyr Phe Ala Met Asp Tyr Trp Gly Gln Gly Thr Leu Val Thr Val Ser Ser SEQ ID NO: 9 - Humanised VH domain (artificial)
Glu Val Gln Leu Val Glu Ser Gly Ala Glu Val Lys Lys Pro Gly Ala Ser Val Lys Val Ser Cys Lys Ala Ser Gly Tyr Ser Phe Ser Gly Tyr Thr Met Asn Trp Val Arg Gln Ala Pro Gly Gln Arg Leu Glu Trp Ile Gly Leu Ile Asn Pro Tyr Asn Gly Gly Thr Ser Tyr Asn Gln Asn Phe Lys Gly Arg Val Thr Leu Thr Val Asp Thr Ser Ala Ser Thr Ala Tyr Leu Glu Leu Asn Ser Leu Arg Ser Glu Asp Thr Gly Val Tyr Tyr Cys Ala Arg Glu Asp Tyr Asp Gly Tyr Leu Tyr Phe Ala Met Asp Tyr Trp Gly Gln Gly Thr Leu Val Thr Val Ser Ser SEQ ID NO: 10 - Humanised VH domain (artificial)
Glu Val Gln Leu Val Glu Ser Gly Ala Glu Val Lys Lys Pro Gly Ala Ser Val Lys Val Ser Cys Lys Ala Ser Gly Tyr Ser Phe Thr Gly Tyr Thr Met Asn Trp Val Arg Gln Ala Pro Gly Gln Arg Leu Glu Trp Ile Gly Leu Ile Asn Pro Tyr Asn Gly Gly Thr Ser Tyr Asn Gln Asn Phe Lys Gly Arg Val Thr Leu Thr Arg Asp Thr Ser Ala Ser Thr Ala Tyr Leu Glu Leu Asn Ser Leu Arg Ser Glu Asp Thr Gly Val Tyr Tyr Cys Ala Arg Glu Asp Tyr Asp Gly Tyr Leu Tyr Phe Ala Met Asp Tyr Trp Gly Gln Gly Thr Leu Val Thr Val Ser Ser SEQ ID NO: 11 - Humanised VH domain (artificial)
Glu Val Gln Leu Val Glu Ser Gly Ala Glu Val Lys Lys Pro Gly Ala Ser Val Lys Val Ser Cys Lys Ala Ser Gly Tyr Ser -continued Phe Thr Gly Tyr Thr Met Asn Trp Val Arg Gln Ala Pro Gly Gln Arg Leu Glu Trp Ile Gly Leu Ile Asn Pro Tyr Asn Gly Gly Thr Ser Tyr Asn Gln Asn Phe Lys Gly Arg Val Thr Leu Thr Val Asp Thr Ser Ala Ser Thr Ala Tyr Leu Glu Leu Asn Ser Leu Arg Ser Glu Asp Thr Gly Val Tyr Tyr Cys Ala Arg Glu Asp Tyr Asp Gly Tyr Leu Tyr Phe Ala Met Asp Tyr Trp Gly Gln Gly Thr Leu Val Thr Val Ser Ser SEQ ID NO: 12 - Humanised VH domain (artificial)
Glu Val Gln Leu Val Glu Ser Gly Ala Glu Val Lys Lys Pro Gly Ala Ser Val Lys Val Ser Cys Lys Ala Ser Gly Tyr Ser Phe Ser Asp Tyr Thr Met Asn Trp Val Arg Gln Ala Pro Gly Gln Arg Leu Glu Trp Ile Gly Leu Ile Asn Pro Tyr Asn Gly Gly Thr Ser Tyr Asn Gln Asn Phe Lys Gly Arg Val Thr Leu Thr Val Asp Thr Ser Ala Ser Thr Ala Tyr Leu Glu Leu Asn Ser Leu Arg Ser Glu Asp Thr Gly Val Tyr Tyr Cys Ala Arg Glu Asp Tyr Asp Gly Tyr Leu Tyr Phe Ala Met Asp Tyr Trp Gly Gln Gly Thr Leu Val Thr Val Ser Ser SEQ ID NO: 13 - Humanised VH domain (artificial)
Glu Val Gln Leu Val Glu Ser Gly Ala Glu Val Lys Lys Pro Gly Ala Ser Val Lys Val Ser Cys Lys Ala Ser Gly Tyr Ser Phe Thr Asp Tyr Thr Met Asn Trp Val Arg Gln Ala Pro Gly Gln Arg Leu Glu Trp Ile Gly Leu Ile Asn Pro Tyr Asn Gly Gly Thr Ser Tyr Asn Gln Asn Phe Lys Gly Arg Val Thr Leu Thr Arg Asp Thr Ser Ala Ser Thr Ala Tyr Leu Glu Leu Asn Ser Leu Arg Ser Glu Asp Thr Gly Val Tyr Tyr Cys Ala Arg Glu Asp Tyr Asp Gly Tyr Leu Tyr Phe Ala Met Asp Tyr Trp Gly Gln Gly Thr Leu Val Thr Val Ser Ser SEQ ID NO: 14 - Humanised VH domain (artificial)
Glu Val Gln Leu Val Glu Ser Gly Ala Glu Val Lys Lys Pro Gly Ala Ser Val Lys Val Ser Cys Lys Ala Ser Gly Tyr Ser Phe Thr Asp Tyr Thr Met Asn Trp Val Arg Gln Ala Pro Gly Gln Arg Leu Glu Trp Ile Gly Leu Ile Asn Pro Tyr Asn Gly Gly Thr Ser Tyr Asn Gln Asn Phe Lys Gly Arg Val Thr Leu Thr Val Asp Thr Ser Ala Ser Thr Ala Tyr Leu Glu Leu Asn Ser Leu Arg Ser Glu Asp Thr Gly Val Tyr Tyr Cys Ala Arg Glu Asp Tyr Asp Gly Tyr Leu Tyr Phe Ala Met Asp Tyr Trp Gly Gln Gly Thr Leu Val Thr Val Ser Ser SEQ ID NO: 15 - VK domain of 2c3 (Murine)
DIQMTQTTSSLSASLGDRVTISCSASQGISNYLNWYQQKADGTVELLIYYTSS

LHSGVPSRFSGSGSGTDYSLTISNLEPEDIATYYCQQYSKLPYTFGGGTKLEI

K

-continued

SEQ ID NO: 16 - Nucleic acid encoding VK domain of 2c3
GACATCCAGATGACCCAGACCACCTCCAGCCTGAGCGCCAGCCTGGGCG

ACCGGGTGACCATCAGCTGCAGCGCCTCCCAGGGCATCAGCAACTACCT

GAACTGGTATCAGCAGAAGGCCGACGGCACCGTCGAGCTGCTGATCTAC

TACACCAGCAGCCTGCACAGCGGCGTGCCCAGCCGGTTTAGCGGCAGCG

GCTCCGGCACCGACTACAGCCTGACCATCTCCAACCTGGAACCCGAGGA

TATCGCCACCTACTACTGCCAGCAGTACAGCAAGCTGCCCTACACCTTTG

GCGGCGGAACAAAGCTGGAAATCAAG

SEQ ID NO: 17 - VH domain of 2c3 with leader sequence (murine)
MVLSLLYLLTALPGILSEVQLQQSGPELVKPGASMKISCKASGYSFTDYTMN

WVKQSHGKNLEWIGLINPYNGGTSYNQNFKGKATLTVDKSSSTAYMELLSL

TSEDSAVYYCAREGYDGYLYFAMDYWGQGTSVTVSS

SEQ ID NO: 18 - Nucleic acid encoding VH domain of 2c3
ATGGTGCTGTCCCTGCTGTACCTGCTGACCGCCCTGCCCGGCATCCTGAG

CGAGGTGCAGCTGCAGCAGAGCGGCCCTGAGCTGGTGAAGCCTGGCGCC

AGCATGAAGATCAGCTGCAAGGCCAGCGGCTACAGCTTCACCGACTACA

CCATGAACTGGGTGAAGCAGAGCCACGGCAAGAACCTGGAATGGATCG

GCCTGATCAACCCCTACAACGGCGGCACCAGCTACAACCAGAACTTCAA

GGGCAAGGCCACCCTGACCGTGGACAAGAGCAGCAGCACCGCCTACATG

GAACTGCTGTCTCTGACCAGCGAGGACAGCGCCGTGTACTACTGCGCCA

GAGAGGGCTACGACGGCTACCTGTACTTCGCCATGGACTACTGGGGCCA

GGGCACCAGCGTGACCGTGAGCAGC

SEQ ID NO: 19 - AY393094 VH domain (human)
LLLAVLQGVCAEVRLVQSGAEVKKPGESLKISCKASGYSFTSNWIGWVRQM

PGKGLEWIGIIFPGDSDTIYSPSFQGQVTISVDKSINTAYLQWSSLKATDTAM

YYCARQNPPEYSGAYHDGWFDPWGQGTLVIVSS

SEQ ID NO: 20 - Nucleic acid encoding AY393094 VH domain
CTCCTCCTGGCTGTTCTCCAAGGAGTCTGTGCCGAGGTGCGCCTTGTGCA

GTCTGGAGCAGAGGTGAAAAAGCCGGGGGAGTCTCTGAAGATCTCCTGT

AAGGCTTCTGGATACAGTTTTACCAGTAACTGGATCGGCTGGGTGCGCC

AGATGCCCGGGAAAGGCCTGGAGTGGATTGGGATCATCTTTCCTGGTGA

CTCTGATACCATATACAGCCCGTCCTTCCAAGGCCAGGTCACCATTTCAG

TCGACAAGTCCATCAATACCGCCTACCTGCAGTGGAGCAGCCTGAAGGC

CACGGACACCGCCATGTATTACTGTGCGAGACAGAACCCCCCCCGAGTAT

AGTGGCGCATATCATGATGGGTGGTTCGACCCCTGGGGCCAGGGAACCC

TGGTCATCGTCTCCTCA

SEQ ID NO: 21 - RHA VH domain (artificial)
MGSTAILGLLLAVLQGVCAEVRLVQSGAEVKKPGESLKISCKASGYSFTDYT

MNWVRQMPGKGLEWIGLINPYNGGTSYNQNFKGQVTISVDKSINTAYLQW

SSLKATDTAMYYCAREGYDGYLYFAMDYWGQGTLVIVSS

SEQ ID NO: 22 - Nucleic acid encoding RHA VH domain (artificial)
ATGGGGTCAACCGCCATCCTTGGCCTCCTCCTGGCTGTTCTCCAAGGAGT

CTGTGCCGAAGTGCGCCTTGTGCAGTCTGGAGCAGAAGTGAAAAAGCCG

GGGGAGTCTCTGAAGATCTCTTGCAAGGCTTCTGGATACAGTTTTACCGA

```
CTACACCATGAACTGGGTGCGCCAGATGCCCGGGAAAGGCCTGGAGTGG

ATTGGGCTTATTAATCCTTACAATGGTGGTACTAGCTACAACCAGAATTT

CAAGGGCCAAGTCACCATTTCAGTCGACAAGTCCATCAATACCGCCTAC

CTGCAGTGGAGCAGCCTGAAGGCCACGGACACCGCCATGTATTACTGTG

CGAGAGAGGGCTATGATGGTTACCTTACTTTGCTATGGACTACTGGGGC

CAGGGAACCCTGGTCATCGTCTCCTCAG

SEQ ID NO: 23 - AY510106 VK domain (human)
MRVPAQLLGLLLLWLPDTRCDIQMTQSPSSLSASVGDRVTITCRASQGISNY

LAWYQQKPGKVPKLLIYAASTLQSGVPSRFSGSGSGTDFTLTISSLQPEDVAT

YYCQKYNSAPYTFGQGTKLEIK

SEQ ID NO: 24 - Nucleic acid encoding AY510106 VK domain
ATGAGGGTCCCTGCTCAGCTCCTGGGACTCCTGCTGCTCTGGCTCCCAGA

TACCAGATGTGACATCCAGATGACCCAGTCTCCATCCTCCCTGTCTGCAT

CTGTAGGAGACAGAGTCACCATCACTTGCCGGGCGAGTCAGGGCATTAG

CAATTATTTAGCCTGGTATCAGCAGAAACCAGGGAAAGTTCCTAAACTC

CTGATCTATGCTGCATCCACTTTGCAATCAGGGGTCCCATCTCGGTTCAG

CGGCAGTGGATCTGGGACAGATTTCACTCTCACCATCAGCAGCCTGCAG

CCTGAAGATGTTGCAACTTATTACTGTCAAAAGTATAACAGTGCCCCGTA

CACTTTTGGCCAGGGGACCAAGCTGGAGATCAAA

SEQ ID NO: 25 - Humanised 2c3 VK domain RKA (artificial)
MRVPAQLLGLLLLWLPDTRCDIQMTQSPSSLSASVGDRVTITCSASQGISNY

LNWYQQKPGKVPKLLIYYTSSLHSGVPSRFSGSGSGTDFTLTISSLQPEDVAT

YYCQQYSKLPYTFGQGTKLEIK

SEQ ID NO: 26 - Nucleic acid encoding humanised 2c3 VK domain RKA
ATGAGGGTCCCTGCTCAGCTCCTGGGACTCCTGCTGCTCTGGCTCCCAGA

TACCAGATGTGACATCCAGATGACCCAGTCTCCATCCTCCCTGTCTGCAT

CTGTAGGAGACAGAGTCACCATCACTTGCAGTGCATCCCAGGGCATTAG

CAATTATCTGAATTGGTATCAGCAGAAACCAGGGAAAGTTCCTAAACTC

CTGATCTATTACACATCAAGTTTACACTCAGGGGTCCCATCTCGGTTCAG

CGGCAGTGGATCTGGGACAGATTTCACTCTCACCATCAGCAGCCTGCAG

CCTGAAGATGTTGCAACTTATTACTGTCAGCAGTATAGCAAGCTGCCGTA

CACGTTTGGCCAGGGGACCAAGCTGGAGATCAAA

SEQ ID NO: 27 - AJ399823 VH domain (human)
EVQLVESGAEVKKPGASVKVSCKASGYSFSSYGIHWVRQAPGQRLEWMG

WINGGTGFTKYSQNFQGRVTLTRDTSASTAYLELNSLRSEDTGVYYCARDP

YNNYAAELDYWGQGTLVTVSS

SEQ ID NO: 28 - Nucleic acid encoding AJ399823 VH domain (human)
GAGGTGCAGCTGGTGGAGTCTGGGGCTGAGGTGAAGAAGCCTGGGGCCT

CAGTGAAAGTTTCGTGCAAGGCTTCTGGATACTCCTTCAGTAGTTATGGT

ATACATTGGGTGCGCCAGGCCCCCGGACAAAGGCTTGAGTGGATGGGAT

GGATCAACGGTGGCACTGGTTTTACAAAATATTCACAGAATTTTCAGGG

CAGAGTCACCCTAACCAGGGACACTTCCGCGAGCACAGCCTACTTGGAA

CTGAACAGCCTGAGATCTGAAGACACGGGTGTATATTACTGTGCGAGGG
```

-continued
ATCCCTACAATAACTACGCGGCGGAACTTGACTACTGGGGCCAGGGAAC

CCTGGTCACCGTCTCCTCA

SEQ ID NO: 29 - Light Chain CDR1 (murine)
SASQGISNYLN

SEQ ID NO: 30 - Light Chain CDR2 (murine)
YTSSLHS

SEQ ID NO: 31 - Light Chain CDR3 (murine)
QQYSKLPYT

SEQ ID NO: 32 - Heavy Chain CDR1 (murine)
DYTMN

SEQ ID NO: 33 - Heavy Chain CDR3 (murine)
EGYDGYLYFAMDY

SEQ ID NO: 34 - Heavy Chain CDR1 (artificial)
GYTMN

SEQ ID NO: 35 - Heavy Chain CDR2 (murine)
LINPYNGGTSYNQNFKG

SEQ ID NO: 36 - Heavy Chain CDR3 (artificial)
EDYDGYLYFAMDY

SEQ ID NO: 37 VH domain leader sequence:
MGSTAILGLLLAVLQGVCA

SEQ ID NO: 38 - 2C3 VK domain leader sequence:
MRVPAQLLGLLLLWLPDTRC

SEQ ID NO: 39 - Human VL leader sequence:
MDMRVPAQLLGLLLLWLPDTRC

SEQ ID NO: 40 - Nucleic acid encoding RH2.5 R71V (artificial)
ATGGGCAGCACAGCCATTCTGGGCCTGCTGCTGGCCGTGCTGCAGGGCG

TGTGCGCCGAGGTGCAGCTGGTCGAGAGCGGAGCCGAGGTGAAGAAGC

CAGGCGCCAGCGTCAAGGTGTCCTGCAAGGCCAGCGGCTACAGCTTCTC

CGGCTACACCATGAACTGGGTGCGGCAGGCCCCAGGCCAGAGGCTGGAA

TGGATGGGCCTGATCAACCCCTACAACGGCGGCACCAGCTACAACCAGA

ACTTCAAGGGCAGGGTGACACTGACCGTGGATACCAGCGCCAGCACCGC

CTACCTGGAACTGAACAGCCTGAGAAGCGAGGACACCGGCGTGTACTAC

TGCGCCAGAGAGGACTACGACGGCTACCTGTACTTCGCCATGGACTACT

GGGGCCAGGGCACCCTGGTGACCGTGAGCAGC

SEQ ID NO: 41 - Kozak consensus sequence (artificial)
AAGCTTGCCGCCACC

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. An antibody that binds interleukin 25 (IL-25), comprising a VL domain which comprises a VL CDR1, a VL CDR2 and a VL CDR3, and a VH domain which comprises SEQ ID NO: 1:

Glu Val Gln Leu Val Glu Ser Gly Ala Glu Val Lys

Lys Pro Gly Ala Ser Val Lys Val Ser Cys Lys Ala

Ser Gly Tyr Ser Phe Xa1 Xa2 Tyr Thr Met Asn Trp

Val Arg Gln Ala Pro Gly Gln Arg Leu Glu Trp Xa3

Gly Leu Ile Asn Pro Tyr Asn Gly Gly Thr Ser Tyr

Asn Gln Asn Phe Lys Gly Arg Val Thr Leu Thr Xa4

Asp Thr Ser Ala Ser Thr Ala Tyr Leu Glu Leu Asn

Ser Leu Arg Ser Glu Asp Thr Gly Val Tyr Tyr Cys

Ala Arg Glu Xa5 Tyr Asp Gly Tyr Leu Tyr Phe Ala

Met Asp Tyr Trp Gly Gln Gly Thr Leu Val Thr Val

Ser Ser wherein:
Xa1 is Ser or Thr;
Xa2 is Gly, Asp, Ala, Ser, Val, Asn, Lys, Tyr or Met;
Xa3 is Met or Ile;
Xa4 is Val or Arg; and
Xa5 is Asp or Asn.

2. The antibody of claim 1 wherein Xa2 is Gly.

3. The antibody of claim 2 wherein Xa2 is Gly and Xa5 is Asp.

4. The antibody of claim 1 wherein Xa1 is Ser.

5. The antibody of claim 1 wherein Xa1 is Thr.

6. The antibody of claim 1 wherein Xa3 is Met.

7. The antibody of claim 1 wherein Xa3 is Ile.

8. The antibody of claim 1 wherein Xa4 is Val.

9. The antibody of claim 1 wherein Xa4 is Arg.

10. The antibody of claim 1 wherein the residues Xa1-Xa5 are in the following combinations:

```
Kabat Res:                30   31   48   71   96
Position in SEQ ID NO: 1: 30   31   48   72   100
Seq List Res:             Xa1  Xa2  Xa3  Xa4  Xa5

SEQ ID NO: 2              Ser  Gly  Met  Val  Asp
SEQ ID NO: 3              Thr  Gly  Met  Arg  Asp
SEQ ID NO: 4              Ser  Gly  Met  Arg  Asp
SEQ ID NO: 5              Thr  Gly  Met  Val  Asp
SEQ ID NO: 6              Ser  Asp  Met  Val  Asp
SEQ ID NO: 7              Thr  Asp  Met  Arg  Asp
SEQ ID NO: 8              Thr  Asp  Met  Val  Asp
SEQ ID NO: 9              Ser  Gly  Ile  Val  Asp
SEQ ID NO: 10             Thr  Gly  Ile  Arg  Asp
SEQ ID NO: 11             Thr  Gly  Ile  Val  Asp
SEQ ID NO: 12             Ser  Asp  Ile  Val  Asp
SEQ ID NO: 13             Thr  Asp  Ile  Arg  Asp
SEQ ID NO: 14             Thr  Asp  Ile  Val  Asp
```

11. The antibody of claim 1 which comprises a VL domain whose Kabat CDRs 1-3 are as set out as residues 24-34 (SEQ ID NO:29); 50-56 (SEQ ID NO:30) and 89-97 (SEQ ID NO:31) respectively of SEQ ID NO: 15.

12. The antibody of claim 11 wherein the VL domain further includes residues 35-38 of SEQ ID NO: 15 adjacent to CDR1 (SEQ ID NO:29).

13. The antibody of claim 11 wherein the VL domain comprises SEQ ID NO: 15.

14. The antibody of claim 11 wherein the VL domain is humanised.

15. The antibody of claim 14 wherein the VL domain comprises amino acids 21-127 of SEQ ID NO:25.

16. The antibody of claim 1 which is a Fab, F(ab')$_2$, scFv, or Fv antibody fragment.

17. The antibody of claim 1 which comprises an antibody constant region.

18. The antibody of claim 17 wherein the constant region is a human IgG1 or IgG4 constant region.

19. The antibody of claim 17 which comprises a whole antibody.

20. An isolated nucleic acid which comprises a nucleotide sequence encoding the antibody of claim 1.

21. An expression vector comprising the nucleic acid of claim 20 operably linked to a promoter.

22. A host cell carrying the expression vector of claim 21.

23. A method of producing an antibody, the method comprising culturing host cells according to claim 22 under conditions for production of said antibody.

24. A method according to claim 23 further comprising isolating said antibody.

25. A method according to claim 24 further comprising formulating the antibody into a composition including at least one additional component.

26. A composition comprising the antibody of claim 1 and a pharmaceutically acceptable carrier.

27. The composition of claim 26 in the form of a lyophilized powder.

28. A method for the treatment or prevention of asthma, said method comprising administering to a subject in need of treatment an effective amount of the antibody of claim 1.

29. A method for the treatment or prevention of ulcerative colitis, said method comprising administering to a subject in need of treatment an effective amount of the antibody of claim 1.

30. A method of producing an antibody that binds interleukin 25 (IL-25) which comprises:
 (a) providing a VH domain which comprises SEQ ID NO: 1:

```
Glu Val Gln Leu Val Glu Ser Gly Ala Glu Val Lys

Lys Pro Gly Ala Ser Val Lys Val Ser Cys Lys Ala

Ser Gly Tyr Ser Phe Xa1 Xa2 Tyr Thr Met Asn Trp
```

-continued
```
Val Arg Gln Ala Pro Gly Gln Arg Leu Glu Trp Xa3

Gly Leu Ile Asn Pro Tyr Asn Gly Gly Thr Ser Tyr

Asn Gln Asn Phe Lys Gly Arg Val Thr Leu Thr Xa4

Asp Thr Ser Ala Ser Thr Ala Tyr Leu Glu Leu Asn

Ser Leu Arg Ser Glu Asp Thr Gly Val Tyr Tyr Cys

Ala Arg Glu Xa5 Tyr Asp Gly Tyr Leu Tyr Phe Ala

Met Asp Tyr Trp Gly Gln Gly Thr Leu Val Thr Val

Ser Ser
``` wherein:
 Xa1 is Ser or Thr;
 Xa2 is Gly, Asp, Ala, Ser, Val, Asn, Lys, Tyr or Met;
 Xa3 is Met or Ile;
 Xa4 is Val or Arg; and
 Xa5 is Asp or Asn;
 (b) combining said VH domain with a plurality of antibody VL domains, wherein each VL domain comprises a VL CDR1, a VL CDR2 and a VL CDR3, to provide antibody molecules;
 (c) screening said antibody molecules for binding to IL-25; and
 (d) selecting an antibody molecule which binds IL-25.

31. An antibody that binds interleukin 25 (IL-25), comprising a VL domain which comprises a VL CDR1, a VL CDR2 and a VL CDR3, and a VH domain which comprises SEQ ID NO: 2.

32. An antibody that binds interleukin 25 (IL-25), comprising a VL domain which comprises a VL CDR1, a VL CDR2 and a VL CDR3, and a VH domain which comprises SEQ ID NO: 3.

* * * * *

UNITED STATES PATENT AND TRADEMARK OFFICE
CERTIFICATE OF CORRECTION

PATENT NO. : 8,658,169 B2  Page 1 of 1
APPLICATION NO. : 13/121898
DATED : February 25, 2014
INVENTOR(S) : Matthews et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 144 days.

Signed and Sealed this

Twenty-ninth Day of September, 2015

Michelle K. Lee
*Director of the United States Patent and Trademark Office*